(12) United States Patent
Wagner

(10) Patent No.: US 11,168,321 B2
(45) Date of Patent: *Nov. 9, 2021

(54) METHODS OF CREATING AND SCREENING DNA-ENCODED LIBRARIES

(71) Applicant: X-Chem, Inc., Waltham, MA (US)

(72) Inventor: Richard W. Wagner, Cambridge, MA (US)

(73) Assignee: X-Chem, Inc., Waltham, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/147,600

(22) Filed: May 5, 2016

(65) Prior Publication Data

US 2016/0369267 A1 Dec. 22, 2016

Related U.S. Application Data

(63) Continuation of application No. 13/147,910, filed as application No. PCT/US2010/024314 on Feb. 16, 2010, now Pat. No. 9,359,601.

(Continued)

(51) Int. Cl.
*C12N 15/10* (2006.01)
*C40B 50/06* (2006.01)
(Continued)

(52) U.S. Cl.
CPC ..... *C12N 15/1065* (2013.01); *C12N 15/1068* (2013.01); *C40B 40/08* (2013.01); *C40B 50/06* (2013.01); *C40B 70/00* (2013.01); *C07H 21/00* (2013.01); *C40B 40/04* (2013.01); *C40B 40/06* (2013.01)

(58) Field of Classification Search
CPC ................ C07H 21/00; C12N 15/1065; C12N 15/1068; C40B 40/04; C40B 40/06; C40B 40/08; C40B 50/06; C40B 70/00
See application file for complete search history.

(56) References Cited

U.S. PATENT DOCUMENTS 5,013,830 A 5/1991 Ohtsuka et al.
5,476,930 A 12/1995 Letsinger et al.
(Continued)

FOREIGN PATENT DOCUMENTS

CN 1898257 A 1/2007
DE 19646372 C1 6/1997
(Continued)

OTHER PUBLICATIONS

Liang et al., "A supra-photoswitch involving sandwiched DNA base pairs and azobenzenes for light-driven nanostructures and nanodevices," Small. 5(15):1761-8 (2009).

(Continued)

*Primary Examiner* — Jeremy C Flinders
(74) *Attorney, Agent, or Firm* — Clark & Elbing LLP

(57) ABSTRACT

The present invention features a number of methods for identifying one or more compounds that bind to a biological target. The methods include synthesizing a library of compounds, wherein the compounds contain a functional moiety having one or more diversity positions. The functional moiety of the compounds is operatively linked to an initiator oligonucleotide that identifies the structure of the functional moiety.

27 Claims, 16 Drawing Sheets

Specification includes a Sequence Listing.

Related U.S. Application Data

(60) Provisional application No. 61/152,508, filed on Feb. 13, 2009.

(51) Int. Cl.

| | |
|---|---|
| *C40B 70/00* | (2006.01) |
| *C07H 21/00* | (2006.01) |
| *C40B 40/06* | (2006.01) |
| *C40B 40/08* | (2006.01) |
| *C40B 40/04* | (2006.01) |

(56) References Cited

U.S. PATENT DOCUMENTS

| | | |
|---|---|---|
| 5,525,734 A | 6/1996 | Gallop et al. |
| 5,525,735 A | 6/1996 | Gallop et al. |
| 5,571,677 A | 11/1996 | Gryaznov |
| 5,571,903 A | 11/1996 | Gryaznov |
| 5,573,905 A | 11/1996 | Lerner et al. |
| 5,585,481 A | 12/1996 | Arnold, Jr. et al. |
| 5,604,097 A | 2/1997 | Brenner |
| 5,633,360 A | 5/1997 | Bischofberger et al. |
| 5,635,400 A | 6/1997 | Brenner |
| 5,639,603 A | 6/1997 | Dower et al. |
| 5,654,413 A | 8/1997 | Brenner |
| 5,656,739 A | 8/1997 | Cubicciotti |
| 5,670,633 A | 9/1997 | Cook et al. |
| 5,681,943 A | 10/1997 | Letsinger et al. |
| 5,695,934 A | 12/1997 | Brenner |
| 5,696,251 A † | 12/1997 | Arnold |
| 5,708,153 A | 1/1998 | Dower et al. |
| 5,723,289 A | 3/1998 | Eaton et al. |
| 5,723,598 A | 3/1998 | Lerner et al. |
| 5,763,175 A | 6/1998 | Brenner |
| 5,770,358 A | 6/1998 | Dower et al. |
| 5,770,367 A | 6/1998 | Southern et al. |
| 5,770,455 A | 6/1998 | Cargill et al. |
| 5,780,231 A | 7/1998 | Brenner |
| 5,780,613 A | 7/1998 | Letsinger et al. |
| 5,789,162 A | 8/1998 | Dower et al. |
| 5,807,683 A | 9/1998 | Brenner |
| 5,840,485 A | 11/1998 | Lebl et al. |
| 5,846,719 A | 12/1998 | Brenner et al. |
| 5,846,839 A | 12/1998 | Gallop et al. |
| 5,863,722 A | 1/1999 | Brenner |
| 5,888,737 A | 3/1999 | DuBridge et al. |
| 5,942,609 A | 8/1999 | Hunkapiller et al. |
| 5,958,691 A | 9/1999 | Pieken et al. |
| 5,962,228 A | 10/1999 | Brenner |
| 6,013,445 A | 1/2000 | Albrecht et al. |
| 6,027,890 A | 2/2000 | Ness et al. |
| 6,060,596 A | 5/2000 | Lerner et al. |
| 6,087,112 A | 7/2000 | Dale |
| 6,090,912 A | 7/2000 | Lebl et al. |
| 6,117,976 A | 9/2000 | Neri et al. |
| 6,140,489 A | 10/2000 | Brenner |
| 6,140,493 A | 10/2000 | Dower et al. |
| 6,143,497 A | 11/2000 | Dower et al. |
| 6,150,516 A | 11/2000 | Brenner et al. |
| 6,165,717 A | 12/2000 | Dower et al. |
| 6,172,214 B1 | 1/2001 | Brenner |
| 6,172,218 B1 | 1/2001 | Brenner |
| 6,214,553 B1 | 4/2001 | Szostak et al. |
| 6,218,111 B1 | 4/2001 | Southern et al. |
| 6,235,475 B1 | 5/2001 | Brenner et al. |
| 6,281,344 B1 | 8/2001 | Szostak et al. |
| 6,329,177 B1 | 12/2001 | Havlina |
| 6,352,828 B1 | 3/2002 | Brenner |
| 6,368,874 B1 | 4/2002 | Gallop et al. |
| 6,406,848 B1 | 6/2002 | Bridgham et al. |
| 6,416,949 B1 | 7/2002 | Dower et al. |
| 6,479,262 B1 | 11/2002 | Delagrave |
| 6,503,759 B1 | 1/2003 | Still et al. |
| 6,537,776 B1 | 3/2003 | Short |
| 6,537,803 B1 | 3/2003 | Amara et al. |
| 6,576,426 B2 | 6/2003 | Southern et al. |
| 6,607,878 B2 | 8/2003 | Sorge |
| 6,627,748 B1 | 9/2003 | Ju et al. |
| 6,654,505 B2 | 11/2003 | Bridgham et al. |
| 6,706,481 B2 | 3/2004 | Rajendran et al. |
| 6,806,052 B2 | 10/2004 | Bridgham et al. |
| 6,831,994 B2 | 12/2004 | Bridgham et al. |
| 6,844,324 B1 | 1/2005 | Zhang et al. |
| 6,846,655 B1 | 1/2005 | Wagner et al. |
| 6,867,290 B2 | 3/2005 | Goldsborough |
| 6,875,736 B2 | 4/2005 | Rana |
| 6,936,467 B2 | 8/2005 | Kmiec et al. |
| 6,936,477 B2 | 8/2005 | Still et al. |
| 6,994,963 B1 | 2/2006 | Murphy et al. |
| 7,033,753 B1 | 4/2006 | Kool |
| RE39,545 E | 4/2007 | Cargill |
| RE39,571 E | 4/2007 | Cargill |
| RE39,606 E | 5/2007 | Cargill |
| 7,217,522 B2 | 5/2007 | Brenner |
| RE39,793 E | 8/2007 | Brenner |
| 7,282,370 B2 | 10/2007 | Bridgham et al. |
| 7,365,179 B2 | 4/2008 | Brenner |
| 7,393,665 B2 | 7/2008 | Brenner |
| 7,407,757 B2 | 8/2008 | Brenner |
| 7,413,536 B1 | 8/2008 | Dower et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,537,897 B2 | 5/2009 | Brenner et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,749,699 B2 | 7/2010 | Kool |
| 7,771,935 B2 | 8/2010 | Liu et al. |
| 7,915,201 B2 | 3/2011 | Franch et al. |
| 7,935,658 B2 | 5/2011 | Morgan et al. |
| 7,972,992 B2 | 7/2011 | Morgan et al. |
| 7,972,994 B2 | 7/2011 | Morgan et al. |
| 7,989,395 B2 | 8/2011 | Morgan et al. |
| 7,998,673 B2 | 8/2011 | French et al. |
| RE43,097 E | 1/2012 | Albrecht et al. |
| 8,148,068 B2 | 4/2012 | Brenner |
| 8,206,901 B2 | 6/2012 | Freskgard et al. |
| 8,361,713 B2 | 1/2013 | Bridgham et al. |
| 8,722,583 B2 | 5/2014 | Gouliaev et al. |
| 2001/0031475 A1 | 10/2001 | Gallop et al. |
| 2002/0034732 A1 | 3/2002 | Capon et al. |
| 2002/0072887 A1 | 6/2002 | Szalma et al. |
| 2003/0049616 A1 | 3/2003 | Brenner et al. |
| 2003/0059826 A1 | 3/2003 | Janda et al. |
| 2003/0119051 A1 | 6/2003 | Wiessler et al. |
| 2003/0143561 A1 | 7/2003 | Pedersen et al. |
| 2003/0187240 A1 | 10/2003 | Cook et al. |
| 2003/0215846 A1 | 11/2003 | Watt et al. |
| 2004/0014090 A1 | 1/2004 | Neri et al. |
| 2004/0049008 A1 | 3/2004 | Pedersen et al. |
| 2004/0083427 A1 | 4/2004 | Wada |
| 2004/0259102 A1 | 12/2004 | Kool |
| 2005/0059049 A1 † | 3/2005 | Moen, Jr. |
| 2005/0100968 A1 | 5/2005 | Gallop et al. |
| 2005/0153321 A1 | 7/2005 | Saba |
| 2005/0158765 A1 | 7/2005 | Morgan et al. |
| 2005/0176948 A1 | 8/2005 | Gouliaev et al. |
| 2005/0221316 A1 | 10/2005 | Pedersen et al. |
| 2005/0221318 A1 | 10/2005 | Gouliaev et al. |
| 2005/0227281 A1 | 10/2005 | Liu et al. |
| 2005/0247001 A1 | 11/2005 | Gouliaev et al. |
| 2005/0255491 A1 | 11/2005 | Lee et al. |
| 2006/0099589 A1 | 5/2006 | Pedersen et al. |
| 2006/0099592 A1 | 5/2006 | Freskgard et al. |
| 2006/0099626 A1 | 5/2006 | Harbury et al. |
| 2006/0115829 A1 | 6/2006 | Mao et al. |
| 2006/0121470 A1 | 6/2006 | Pedersen |
| 2006/0154246 A1 | 7/2006 | Neri et al. |
| 2006/0160125 A1 | 7/2006 | Kool |
| 2006/0166197 A1 | 7/2006 | Gouliaev et al. |
| 2006/0177833 A1 | 8/2006 | Brenner |
| 2006/0193869 A1 | 8/2006 | Barrat et al. |

(56) References Cited

U.S. PATENT DOCUMENTS

| | | |
|---|---|---|
| 2006/0199192 A1 | 9/2006 | Kool et al. |
| 2006/0211030 A1 | 9/2006 | Brenner |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0022460 A1 | 1/2007 | Kim et al. |
| 2007/0026397 A1 | 2/2007 | Freskgard et al. |
| 2007/0042401 A1 | 2/2007 | Morgan et al. |
| 2007/0213519 A1 | 9/2007 | Gouliaev et al. |
| 2007/0224607 A1† | 9/2007 | Morgan |
| 2008/0193983 A1 | 8/2008 | Gouliaev et al. |
| 2008/0220982 A1 | 9/2008 | Vu |
| 2008/0305957 A1 | 12/2008 | Thisted et al. |
| 2008/0318802 A1 | 12/2008 | Brenner |
| 2009/0005256 A1 | 1/2009 | Bittker et al. |
| 2009/0011957 A1 | 1/2009 | Gouliaev et al. |
| 2009/0035824 A1 | 2/2009 | Liu et al. |
| 2009/0062147 A1 | 3/2009 | Morgan et al. |
| 2009/0143232 A1 | 6/2009 | Pedersen et al. |
| 2009/0143244 A1 | 6/2009 | Bridgham et al. |
| 2009/0239211 A1 | 9/2009 | Freskgard et al. |
| 2009/0239768 A1 | 9/2009 | Hansen et al. |
| 2009/0264300 A1 | 10/2009 | Franch et al. |
| 2010/0016177 A1 | 1/2010 | Pedersen et al. |
| 2010/0094036 A1 | 4/2010 | Hirata et al. |
| 2010/0159526 A1 | 6/2010 | Jendrisak et al. |
| 2010/0184611 A1 | 7/2010 | Neri et al. |
| 2010/0184661 A1 | 7/2010 | Luo et al. |
| 2011/0003290 A1 | 1/2011 | Gale et al. |
| 2011/0104785 A1 | 5/2011 | Vaidyanathan et al. |
| 2011/0136697 A1 | 6/2011 | Morgan et al. |
| 2011/0183863 A1 | 7/2011 | Wagner et al. |
| 2011/0251089 A1 | 10/2011 | Morgan et al. |
| 2011/0262898 A1 | 10/2011 | Dong et al. |
| 2011/0319278 A1 | 12/2011 | Neri et al. |
| 2012/0004137 A1 | 1/2012 | Wagner et al. |
| 2012/0053091 A1 | 3/2012 | Wagner |
| 2012/0071329 A1 | 3/2012 | Morgan et al. |
| 2012/0107840 A1 | 5/2012 | Wagner et al. |
| 2012/0245040 A1 | 9/2012 | Morgan et al. |
| 2013/0046084 A1 | 2/2013 | Brown et al. |
| 2013/0102545 A1 | 4/2013 | Gao et al. |
| 2013/0237459 A1 | 9/2013 | Rasmussen |
| 2013/0281324 A1 | 10/2013 | Gouliaev et al. |
| 2014/0315762 A1 | 10/2014 | Keefe et al. |

FOREIGN PATENT DOCUMENTS

| | | |
|---|---|---|
| DE | 19642751 A1 | 4/1998 |
| EP | 0928290 B1 | 3/2005 |
| EP | 1533385 A1 | 5/2005 |
| EP | 1423400 B1 | 8/2006 |
| EP | 1905829 A2 | 4/2008 |
| EP | 1828381 B1 | 1/2009 |
| EP | 2175019 A2 | 4/2010 |
| EP | 2186897 A1 | 5/2010 |
| EP | 2236606 A2 | 10/2010 |
| EP | 1957644 B1 | 12/2010 |
| EP | 2258870 A2 | 12/2010 |
| EP | 2305808 A1 | 4/2011 |
| EP | 2311786 A2 | 4/2011 |
| EP | 1558744 B1 | 6/2011 |
| EP | 2336315 A2 | 6/2011 |
| EP | 2338990 A2 | 6/2011 |
| EP | 2341140 A1 | 7/2011 |
| EP | 2348124 A2 | 7/2011 |
| EP | 2348125 A2 | 7/2011 |
| EP | 2216338 B1 | 3/2013 |
| EP | 2272856 B1 | 11/2015 |
| EP | 3351631 A2 | 7/2018 |
| EP | 3211126 B1 | 10/2020 |
| GB | 9315847.5 | 7/1993 |
| JP | 5292967 A | 11/1993 |
| JP | 8000268 A | 1/1996 |
| JP | 2002315577 A | 10/2002 |
| JP | 2007-529994 A | 11/2007 |
| WO | WO-92/22875 A1 | 12/1992 |
| WO | WO-93/06121 A1 | 4/1993 |
| WO | WO-93/20242 A1 | 10/1993 |
| WO | WO-94/08051 A1 | 4/1994 |
| WO | WO-95/04160 A1 | 2/1995 |
| WO | WO-95/06293 A1 | 3/1995 |
| WO | WO-95/12608 A1 | 5/1995 |
| WO | WO-96/35699 A1 | 11/1996 |
| WO | WO-96/38726 A1 | 12/1996 |
| WO | WO-97/32999 A1 | 9/1997 |
| WO | WO-98/04575 A2 | 2/1998 |
| WO | WO-98/31700 A1 | 7/1998 |
| WO | WO-99/10485 A1 | 3/1999 |
| WO | WO-99/18240 A1 | 4/1999 |
| WO | WO-00/20639 A1 | 4/2000 |
| WO | WO-00/23458 A1 | 4/2000 |
| WO | WO-00/32823 A1 | 6/2000 |
| WO | WO-00/61775 A1 | 10/2000 |
| WO | WO-01/16352 A1 | 3/2001 |
| WO | WO-02/40664 A1 | 5/2002 |
| WO | WO-02/074929 A2 | 9/2002 |
| WO | 02103008 † | 12/2002 |
| WO | WO-02/102820 A1 | 12/2002 |
| WO | WO-02/103008 A2 | 12/2002 |
| WO | WO-03/078050 A2 | 9/2003 |
| WO | WO-03/078445 A2 | 9/2003 |
| WO | WO-03/078446 A2 | 9/2003 |
| WO | WO-03/078625 A2 | 9/2003 |
| WO | WO-03/078626 A2 | 9/2003 |
| WO | WO-03/078627 A2 | 9/2003 |
| WO | WO-2004/001042 A2 | 12/2003 |
| WO | WO-2004/009814 A1 | 1/2004 |
| WO | WO-2004/013070 A2 | 2/2004 |
| WO | WO-2004/016767 A2 | 2/2004 |
| WO | WO-2004/024929 A2 | 3/2004 |
| WO | 2004039825 † | 5/2004 |
| WO | WO-2004/039825 A2 | 5/2004 |
| WO | WO-2004/056994 A2 | 7/2004 |
| WO | 2004083427 † | 9/2004 |
| WO | WO-2004/074429 A2 | 9/2004 |
| WO | WO-2004/074501 A2 | 9/2004 |
| WO | WO-2004/083427 A2 | 9/2004 |
| WO | WO-2005/008240 A2 | 1/2005 |
| WO | WO-2005/026387 A1 | 3/2005 |
| WO | WO-2005/058479 A2 | 6/2005 |
| WO | WO-2005/078122 A2 | 8/2005 |
| WO | WO-2005/090566 A2 | 9/2005 |
| WO | WO-2006/048025 A1 | 5/2006 |
| WO | WO-2006/053571 A2 | 5/2006 |
| WO | WO-2006/079061 A2 | 7/2006 |
| WO | WO-2006/135786 A2 | 12/2006 |
| WO | WO-2007/041201 A2 | 4/2007 |
| WO | WO-2007/053358 A2 | 5/2007 |
| WO | WO-2007/062664 A2 | 6/2007 |
| WO | WO-2009/066447 A1 | 5/2009 |
| WO | WO-2009/077173 A2 | 6/2009 |
| WO | WO-2009/152824 A1 | 12/2009 |
| WO | WO-2010/086602 A1 | 8/2010 |
| WO | WO-2010/094027 A1 | 8/2010 |
| WO | WO-2010/094036 A1 | 8/2010 |
| WO | WO-2010/094040 A1 | 8/2010 |
| WO | WO-2011/005762 A1 | 1/2011 |
| WO | WO-2011/120042 A1 | 9/2011 |
| WO | WO-2011/127933 A1 | 10/2011 |
| WO | WO-2012/125733 A2 | 9/2012 |
| WO | WO-2013/036810 A1 | 3/2013 |
| WO | WO-2014/012010 A1 | 1/2014 |
| WO | WO-2015/091207 A1 | 6/2015 |

OTHER PUBLICATIONS

Notification of Material filed by a Third Party for Australian Patent Application No. 2012304387, dated Feb. 16, 2017 (44 pages).

Notification of Third-Party Submission of Information and English Translation for Japanese Patent Application No. 2014-529907, dated Jan. 16, 2017 (2 pages).

(56) References Cited

OTHER PUBLICATIONS

Third-Party Observation pursuant to Art. 115 EPC for European Patent Application No. 10741877, dated Feb. 16, 2017 (28 pages).
Zietlow et al., "DNA polymerase I-mediated translesion synthesis in RecA-independent DNA interstrand cross-link repair in E. coli," Biochemistry. 47(19):5460-4 (2008).
Office Action for Canadian Patent Application No. 2,752,543, dated Jul. 4, 2016 (4 pages).
Sastry et al., "Cross-linking of DNA-binding proteins to DNA with psoralen and psoralen furan-side monoadducts. Comparison of action spectra with DNA-DNA cross-linking," J Biol Chem. 272(6):3715-23 (1997).
Pre-Issuance Submission by Third-Party for U.S. Appl. No. 14/343,306, filed May 25, 2016 (22 pages).
Office Action and English Translation for Chinese Patent Application No. 2010800078133, dated Jan. 3, 2017 (22 pages).
"Substantial Background Reduction in Ligase-based Apoptosis Detection Using Newly Designed Hairpin Oligoprobes," available in PMC Jun. 18, 2007, published in final edited form as: Biotechniques. 27:1130-2 (1999) (5 pages).
Abe et al., "Structure analysis of oligonucleotide in organic solvent," Nucleic Acids Symposium Series. 50:25-6 (2006).
Amato, "Speeding up a chemical game of chance," Science. 257(5068):330-1 (1992).
Anonymous, "Non-enzymatic ligation of single-stranded and duplex DNA," Glen Research Report of Products for RNA and DNA Oligonucleotide Synthesis. 10 (1997). (1 page).
Balanov et al., "Development of DNA-encoded library containing $10^9$ backbone cyclic peptides on 7µM glass beads," Peptides Frontiers of Peptide Science, American Peptide Symposia. 5:49-50 (2002).
Bartel et al., "Isolation of new ribozymes from a large pool of random sequences," Science. 261(5127):1411-8 (1993).
Berezovski et al., "Non-SELEX: selection of aptamers without intermediate amplification of candidate oligonucleotides," Nat Protoc. 1(3):1359-69 (2006).
Brenner et al., "Encoded combinatorial chemistry," Proc Natl Acad Sci U.S.A. 89(12):5381-3 (1992).
Brenner et al., "Gene expression analysis by massively parallel signature sequencing (MPSS) on microbead arrays," Nat Biotechnol. 18(6): 630-4 (2000).
Brenner et al., "In vitro cloning of complex mixtures of DNA on microbeads: physical separation of differentially expressed cDNAs," Proc Natl Acad Sci U.S.A. 97(4): 1665-70 (2000).
Bruick et al., "Template-directed ligation of peptides to oligonucleotides," Chem Biol. 3(1):49-56 (1996).
Cherepanov et al., "Scanning mutagenesis using T4 DNA ligase and short degenerate DNA oligonucleotides containing tri-nucleotide mismatches," J Biochem. 132(1):143-7 (2002).
Chiu et al., "Visualizing a correlation between siRNA localization, cellular uptake, and RNAi in living cells," Chem Biol. 11(8):1165-75 (2004).
Clark et al., "Design, synthesis and selection of DNA-encoded small-molecule libraries," Nat Chem Biol. 5(9):647-54 (2009).
Ekland et al., "Structurally complex and highly active RNA ligases derived from random RNA sequences," Science. 269(5222):364-70 (1995).
Extended European Search Report for European Patent Application No. 10741870.9, dated Jul. 10, 2012 (12 pages).
Extended European Search Report for European Patent Application No. 10741877.4, dated Jun. 27, 2012 (8 pages).
File History for European Patent Application No. 03757752.5 (1,559 pages).
File History for U.S. Appl. No. 10/525,817 mailed May 1, 2011 (735 pages).
Gartner et al., "The generality of DNA-templated synthesis as a basis for evolving non-natural small molecules," J Am Chem Soc. 123(28):6961-3 (2001).
Goodwin et al., "Template-directed synthesis: use of a reversible reaction," J Am Chem Soc. 114(23):9197-8 (1992).

Géron-Landre et al., "Sequence-specific fluorescent labeling of double-stranded DNA observed at the single molecule level," Nucleic Acids Res. 31(20):e125 (2003) (8 pages).
Halpin et al., "DNA display I. Sequence-encoded routing of DNA populations," PLoS Biol. 2(7):E173 (2004) (7 pages).
Halpin et al., "DNA display II. Genetic manipulation of combinatorial chemistry libraries for small-molecule evolution," PLoS Biol. 2(7):E174 (2004) (9 pages).
Harada et al., "In vitro selection of optimal DNA substrates for T4 RNA ligase," Proc Natl Acad Sci U.S.A. 90(4):1576-9 (1993).
Herrlein et al., "A covalent lock for self-assembled oligonucleotide conjugates," J Am Chem Soc. 117(40):10151-2 (1995).
International Search Report and Written Opinion for International Patent Application No. PCT/US2010/024296, dated Jun. 10, 2010 (11 pages).
International Search Report and Written Opinion for International Patent Application No. PCT/US2010/024314, dated May 7, 2010 (6 pages).
International Search Report and Written Opinion for International Patent Application No. PCT/US2012/054228, dated Jan. 7, 2013 (9 pages).
Ito et al., "Modification of lipase with various synthetic polymers and their catalytic activities in organic solvent," Biotechnol Prog. 10(4):398-402 (1994).
Janda, "Tagged versus untagged libraries: methods for the generation and screening of combinatorial chemical libraries," Proc Natl Acad Sci U.S.A. 91(23):10779-85 (1994).
Jarosch et al., "In vitro selection using a dual RNA library that allows primerless selection," Nucleic Acids Res. 34(12):e86 (2006) (9 pages).
Jenne et al., "A novel ribozyme with ester transferase activity," Chem Biol. 5(1):23-34 (1998).
Jäschke et al., "Synthesis and properties of oligodeoxyribonucleotide-polyethylene glycol conjugates," Nucleic Acids Res. 22(22):4810-7 (1994).
Kempe et al., "Chemical and enzymatic biotin-labeling of oligodeoxyribonucleotides," Nucleic Acids Res. 13(1):45-57 (1985).
Kinoshita et al., "Enzymatic synthesis of code regions for encoded combinatorial chemistry (ECC)," Nucleic Acids Symp Ser. 34:201-2 (1995).
Kinoshita et al., "Enzymatic synthesis of sequencing primers based on a library of tetramers," Chem Express. 7:149-52 (1992).
Kinoshita et al., "Strand ligation in a double-stranded DNA by T4 RNA ligase," Chem Lett. 9:797-8 (1996).
Kitamura et al., "Construction of block-shuffled libraries of DNA for evolutionary protein engineering: Y-ligation-based block shuffling," Protein Eng. 15(10):843-53 (2002).
Kitamura et al., "Development of systemic in vitro evolution and its application to generation of peptide-aptamer-based inhibitors of cathepsin E," J Mol Biol. 387(5):1186-98 (2009).
Lebl, "Parallel personal comments on "classical" papers in combinatorial chemistry," J Comb Chem. 1(1):3-24 (1999).
Lee et al., "Ribozyme-catalyzed tRNA aminoacylation," Nat Struct Biol. 7(1):28-33 (2000).
Li et al., "Kinetics of RNA degradation by specific base catalysis of transesterification involving the 2'-hydroxyl group," J Am Chem Soc. 121(23):5364-72 (1999).
Lipinski et al., "Experimental and computational approaches to estimate solubility and permeability in drug discovery and development settings," Adv Drug Deliv Rev. 46(1-3):3-26 (2001).
Liu, "Development of amplifiable and evolvable unnatural molecules," website of Dr. D. R. Liu, publicly <http://web.archive.ora/web/20000311112631/http://evolve.havard.edu> retreived May 9, 2007 (2 pages).
Liu, "The chemistry and chemical biology of molecular evolution," website of Dr. D.R. Liu, <http://web.archive.org/web/20010301175107/http://evolve.havard edu>, retrieved Sep. 5, 2007 (2 pages).
Liu, "The Chemistry of Molecular Evolution," website of Dr. D.R. Liu <http://web.archive.ora/web/20001015144553/http://evolve. havard.edu>, retrieved Sep. 5, 2007 (3 pages).

(56) References Cited

OTHER PUBLICATIONS

Morpurgo et al., "An approach to increased polyplex gene delivery by peptides selected from a phage display library," J Biochem Biophys Methods. 52(1):31-43 (2002).
Needels et al., "Generation and screening of an oligonucleotide-encoded synthetic peptide library," Proc Natl Acad Sci U.S.A. 90(22):10700-4 (1993).
Nielsen et al., "Synthetic methods for the implementation of encoded combinatorial chemistry," J Am Chem Soc. 115(12):9812-3 (1993).
Nielsen et al., "Toward chemical implementation of encoded combinatorial libraries," Methods. 6(4):361-71 (1994).
Nishigaki et al., "T4 RNA ligase: Its potential and applications to molecular biotechnology," Symp Biofunc Chem. 13:394-6 (1998) (5 pages).
Nishigaki et al., "Y-ligation: An efficient method for ligating single-stranded DNAs and RNAs with T4 RNA ligase," Mol Divers. 4(3):187-90 (1998).
Nishigaki, "RNA Ligases," Encyclopedia of Molecular Biology (2002) (3 pages).
Office Action for Canadian Patent Application No. 2,752,543, dated Nov. 30, 2015 (4 pages).
Office Action for Chinese Patent Application No. 2012800539302, dated Jan. 28, 2015 (14 pages).
Pochet et al., "Solid-supported ligation primer," Nucleic Acids Res. 16(4):1619 (1988).
Roberts et al., "RNA-peptide fusions for the in vitro selection of peptides and proteins," Proc Natl Acad Sci U.S.A. 94(23):12297-302 (1997).
Rohatgi et al., "Kinetic and mechanistic analysis of nonenzymatic, template-directed oligoribonucleotide ligation," J Am Chem Soc. 118(14):3332-9 (1996).
Rohatgi et al., "Nonenzymatic, template-directed ligation of oligoribonucleotides is highly regioselective for the formation of 3'-5' phosphodiester bonds," J Am Chem Soc. 118(14):3340-4 (1996).
Rozenman et al., "DNA-templated synthesis in organic solvents," Chembiochem. 7(2):253-6 (2006).
Scheuermann et al., "DNA-encoded chemical libraries," J Biotechnol. 126(4):568-81 (2006).
Schmidt et al., "Information transfer from DNA to peptide nucleic acids by template-directed syntheses," Nucleic Acids Res. 25(23):4792-6 (1997).
Schmitz et al., "Solid-phase enzymatic synthesis of oligonucleotides," Org Lett. 1(11):1729-31 (1999).
Search Report and Written Opinion for Singaporean Application No. 11201400374T, completed Jan. 5, 2015 (19 pages).
Stryer, "Eukaryotic Chromosomes and Gene Expression," Biochemistry, W.H. Freeman and Company: New York, 4th ed., 975-88 (1995).
Suga et al., "Structural and kinetic characterization of an acyl transferase ribozyme," J Am Chem Soc. 120(6):1151-6 (1998).
Suga et al., "Unusual metal ion catalysis in an acyl-transferase ribozyme," Biochemistry. 37(28):10118-25 (1998).
Summerer et al., "DNA-templated synthesis: more versatile than expected," Angew Chem Int Ed Engl. 41(1):89-90 (2002).
Supplementary Methods for Clark et al., "Design, Synthesis and selection of DNA-encoded small molecule libraries," Nat Chem Biol. 5(9):1-57 (2009).
Tabuchi et al., "An efficient ligation method in the making of an in vitro Virus for in vitro Protein evolution," Biol Proced Online. 4:49-54 (2002).
Tamura et al., "Oligonucleotide-directed peptide synthesis in a ribosome- and ribozyme-free system," Proc Natl Acad Sci U.S.A. 98(4):1393-7 (2001).
Tessier et al., "Ligation of single-stranded oligodeoxyribonucleotides by T4 RNA ligase," Anal Biochem. 158(1):171-8 (1986).
Visscher et al., "Template-directed synthesis of acyclic oligonucleotide analogues," J Mol Evol. 28(1-2):3-6 (1988).

Walder et al., "Complementary carrier peptide synthesis: general strategy and implications for prebiotic origin of peptide synthesis," Proc Nat Acad Sci U.S.A. 76(1):51-5 (1979).
Xu et al., "Chemical and enzymatic properties of bridging 5'-S-phosphorothioester linkages in DNA," Nucleic Acids Res. 26(13):3159-64 (1998).
Xu et al., "High sequence fidelity in a non-enzymatic DNA autoligation reaction," Nucleic Acids Res. 27(3):875-81 (1999).
Yoshimura et al.,"Ultrafast reversible photo-cross-linking reaction: toward in situ DNA manipulation," Org Lett. 10(15):3227-30 (2008).
Zhang et al., "Single-stranded DNA ligation by T4 RNA ligase for PCR cloning of 5'-noncoding fragments and coding sequence of a specific gene," Nucleic Acids Res. 24(5):990-1 (1996).
Third-Party Observation pursuant to Art. 115 EPC for European Patent Application No. 10741877, filed Mar. 14, 2016 (38 pages).
Mullah et al., "Efficient synthesis of double dye-labeled oligodeoxyribonucleotide probes and their application in a real time PCR assay," Nucleic Acids Res. 26(4):1026-031 (1998).
Thelwell et al., "Mode of action and application of Scorpion primers to mutation detection," Nucleic Acids Res. 28(19):3752-61 (2000).
Wagner, "Gene inhibition using antisense oligodeoxynucleotides," Nature. 372:333-5 (1994).
Wagner et al., "Antisense gene inhibition by oligonucleotides containing C-5 propyne pyrimidines," Science. 260:1510-3 (1993).
Yamana et al., "Synthesis and binding properties of oligonucleotides containing an azobenzene linker," Nucleosides and Nucleotides. 17(1-3):233-42 (1998).
Communication pursuant to Article 94(3) EPC for European Patent Application No. 10741877.4, dated Mar. 24, 2016 (6 pages).
Anonymous, "PDC-CE Phosphoramidite," Glen Research Report of Products for RNA and DNA Oligonucleotide Synthesis. (2004) (3 pages).
Anonymous, "PDU-CE Phosphoramidite," Glen Research Report of Products for RNA and DNA Oligonucleotide Synthesis. (2004) (3 pages).
Anonymous, "5-F-DU-CE Phosphoramidite," Glen Research Report of Products for RNA and DNA Oligonucleotide Synthesis. (2004) (3 pages).
Anonymous, "Versatile New Reagents: Pyrene-dU and Perylene-dU," Glen Research Report of Products for RNA and DNA Oligonucleotide Synthesis. (2008) (2 pages).
Korshun et al., "5-(1-pyrenylethynyl)-2'-deoxyuridine, a novel fluorescent nucleoside analog," Bioorg Khim. 22:923-5 (1996).
Search Report and Written Opinion for Singapore Patent Application No. 2014011381, dated Jun. 7, 2016 (8 pages).
Notice of Preliminary Rejection and English translation for Korean Patent Application No. 10-2011-7021196, dated Nov. 29, 2016 (12 pages).
Third-Party Observation pursuant to Art. 115 EPC for European Patent Application No. 12830083, dated Dec. 8, 2016 (51 pages).
Uhlenbeck et al., "2. T4 RNA Ligase," Enzymes. 15:31-58 (1982).
Blondal et al., "Isolation and characterization of a thermostable RNA ligase 1 from a Thermus scotoductus bacteriophage TS2126 with good single-stranded DNA ligation properties," Nucleic Acids Res. 33(1):135-42 (2005).
Tessier et al., "Ligation of single-stranded oligodeoxyribonucleotides by T4 RNA ligase," Anal Biochem. 158:171-8 (1986).
Cummins et al., "Characterization of fully 2'-modified oligoribonucleotide hetero- and homoduplex hybridization and nuclease sensitivity," Nucleic Acids Res. 23(11):2019-24 (1995).
Berger et al., "Chemistry on nucleic acid templates," Chem Biodivers. 7(10):2581-615 (2010).
Dimitri et al., "Transcription elongation past O6-methylguanine by human RNA polymerase II and bacteriophage T7 RNA polymerase," Nucleic Acids Res. 36(20):6459-71 (2008).
El-Sagheer et al., "Click nucleic acid ligation: applications in biology and nanotechnology," Acc Chem Res. 45(8):1258-67 (2012).
El-Sagheer et al., "Efficient RNA synthesis by in vitro transcription of a triazole-modified DNA template," Chem Commun (Camb). 47(44):12057-8 (2011).
Engelhart et al., "Nonenzymatic ligation of DNA with a reversible step and a final linkage that can be used in PCR," Chembiochem. 13(8):1121-4 (2012).

(56) References Cited

OTHER PUBLICATIONS

Fujimoto et al., "A light-controlled reversible DNA photoligation via carbazole-tethered 5-carboxyvinyluracil," Org Lett. 10(3):397-400 (2008).
Hoepfner et al., "Amplified primer extension assay for psoralen photoproducts provides a sensitive assay for a (CG)6TA(CG)2(TG)8 Z-DNA torsionally tuned probe: preferential psoralen photobinding to one strand of a B-Z junction," Biochemistry 32(29):7542-8 (1993).
Leggett et al., "NextClip: an analysis and read preparation tool for Nextera Long Mate Pair libraries," Bioinformatics 30(4):566-8 (2014).
Li et al., "DNA-templated organic synthesis: nature's strategy for controlling chemical reactivity applied to synthetic molecules," Angew Chem Int Ed Engl. 43(37):4848-70 (2004).
Litovchick et al., "Encoded Library Synthesis Using Chemical Ligation and the Discovery of sEH Inhibitors from a 334-Million Member Library," Sci Rep. 5:10916 (2015) (8 pages).
Litovchick et al., "Universal strategies for the DNA-encoding of libraries of small molecules using the chemical ligation of oligonucleotide tags," Artif DNA PNA XNA. 5(1):e27896 (2014) (11 pages).
Nakamura et al., "Template directed reversible photochemical ligation of oligodeoxynucleotides," Molecules 17(1):163-78 (2012).
Ogino et al., "Template-directed DNA photoligation via alpha-5-cyanovinyldeoxyuridine," Org Lett. 7(14):2853-6 (2005).
Paredes et al., "Click chemistry for rapid labeling and ligation of RNA," Chembiochem. 12(1):125-31 (2011).
Qiu et al., "A diazirine-based nucleoside analogue for efficient DNA interstrand photocross-linking," J Am Chem Soc. 130(44):14398-9 (2008).
Tornaletti et al., "Transcription arrest at an abasic site in the transcribed strand of template DNA," Chem Res Toxicol. 19(9):1215-20 (2006).
Yoshimura et al., "Highly selective and sensitive template-directed photoligation of DNA via 5-carbamoylvinyl-2'-deoxycytidine," Org Lett. 8(22):5049-51 (2006).
Extended European Search Report for European Patent Application No. 17163865.3, dated May 17, 2017 (9 pages).
Examination Report for Indian Patent Application No. 6461/CHENP/2011, dated Oct. 13, 2017 (6 pages).
Second Written Opinion for Singaporean Patent Application No. 2014011381, dated Oct. 19, 2017 (8 pages).
Third Party Submission for Canadian Patent Application No. 2752543 dated May 11, 2017 (29 pages).
Communication pursuant to Rule 114(2) EPC for European Patent Application No. 10741877.4, dated Oct. 7, 2016 (29 pages).
Asanuma et al., "Photocontrol of DNA duplex formation by using azobenzene-bearing oligonucleotides," Chembiochem. 2(1):39-44 (2001).
Beaucage et al., "The functionalization of oligonucleotides via phosphoramidite derivatives," Tetrahedron 49(10):1925-63 (1993).
Bonora et al., "Synthesis and characterization of high-molecular mass polyethylene glycol-conjugated oligonucleotides," Bioconjug Chem. 8(6):793-7 (1997).
Cui, "Have the primary structures of biomacromolecules been selected in a Darwinian fashion to adapt to the surrounding environments of our planet?," IUBMB Life 61(8):860-3 (2009).
Efimov et al., "Cross-linked nucleic acids: formation, structure, and biological function," Russ J Bioorg Chem. 36(1):49-72 (2010).
Glen Research Information and MSDS for 5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite (Catalogue No. 10-1039-xx from Apr. 14, 2005 and Aug. 19, 2004), available at: https://web.archive.org/web/20050414005644/http://www.glenresearch.com/ProductFiles/10-1039.html; https://web.archive.org/web/20040819072021/http://www.glenresearch.com/ProductFiles/MSDS/m10-1039.html (4 pages.).
Glen Research Information and MSDS for 5-F-dU-CE Phosphoramidite (Catalogue No. 10-1092-xx from Oct. 28, 2004 and Apr. 28, 2005), available at: https://web.archive.org/web/20050428232151/http://www.glenresearch.com/ProductFiles/10-1092.html; https://web.archive.org/web/20041028091346/http://www.glenresearch.com/ProductFiles/MSDS/m10-1092.html (4 pages).
Glen Research Information and MSDS for pdC-CE Phosphoramidite (Catalogue No. 10-1014-xx from Sep. 1, 2004 and Mar. 8, 2005), available at: https://web.archive.org/web/20050308232245/http://www.glenresearch.com:80/ProductFiles/10-1014.html; https://web.archive.org/web/20040901150244/http://www.glenresearch.com/ProductFiles/MSDS/m10-1014.html (4 pages).
Glen Research Information and MSDS for pdU-CE Phosphoramidite (Catalogue No. 10-1054-xx from Oct. 28, 2004 and Mar. 8, 2005), available at: https://web.archive.org/web/20050308232237/http://www.glenresearch.com/ProductFiles/10-1054.html; https://web.archive.org/web/20041028103548/http://www.glenresearch.com/ProductFiles/MSDS/m10-1054.html (3 pages).
Glen Research Information for Pyrene-dU-CE Phosphoramidite (Catalogue No. 10-1590-xx from Aug. 21, 2008 and Dec. 2, 2008), available at: https://web.archive.org/web/20081202060550/http://www.glenresearch.com/Catalog/structural.html#a101590; https://web.archive.org/web/20080821194747/http://www.glenresearch.com/GlenReports/GR19-28.html (9 pages).
Integrated DNA Technologies, Inc. for "Int Spacer 9" (iSp9—Product No. 1391 from Oct. 16, 2006 and Nov. 9, 2006) available at <https://web.archive.org/web/20071109184957/http://www.idtdna.com:80/Catalog/Modifications/RNAModifications.aspx https://web.archive.org/web/20061016193020/https://www.idtdna.com/catalog/Modifications/Modifications.aspx?ProductID=1391 > (2 pages).
Integrated DNA Technologies, Inc. for "Int Uni-Link™ Amino Modifier" (iUniAmM—Product No. 1440 from Oct. 16, 2006 and Nov. 15, 2006) available at <https://web.archive.org/web/20061115041630/http://www.idtdna.com:80/Catalog/Modifications/RNAModifications.aspxhttps://web.archive.org/web/20061016184659/https://www.idtdna.com/Catalog/Modifications/Modifications.aspx?ProductID=1440> (2 pages).
Jäschke, Chapter 18: Oligonucleotide-Poly(ethylene glycol) Conjugates: Synthesis, Properties, and Applications. *ACS Symposium Series*, p. 265-83 (1997).
Lewis et al., "Synthesis, structure, and photochemistry of exceptionally stable synthetic DNA hairpins with stilbene diether linkers," J Am Chem Soc. 124(41):12165-73 (2002).
Malakhov et al., "Synthesis and fluorescent properties of 5-(1-pyrenylethynyl)-2'-deoxyuridine-containing oligodeoxynucleotides," Russ J Bioorg Chem. 26(1):34-44 (2000).
Notice of Preliminary Rejection for Korean Patent Application No. 10-2017-7029869, dated Feb. 15, 2018 (10 pages).
Polyethylene Glycols. Prepared at the 31st JECFA (1987), published in 1988 in FAO Food and Nutrition Paper 38 (FNP 38), and in 1992 in vol. 3 of "Compendium of Food Additive Specifications" (FNP 52) (11 pages).
Ren et al., "Formation of Stable DNA Loops by Incorporation of Nonpolar, Non-Hydrogen-Bonding Nucleoside Isosteres," Available in PMC Sep. 27, 2010, published in final edited form as: Angew Chem Int Ed Engl. 35(7):743-6 (1996) (8 pages).
Salunkhe et al., "Control of folding and binding of oligonucleotides by use of a nonnucleotide linker," J Am Chem Soc. 114(23):8768-72 (1992).
Supporting information for Rozenman and Liu, ChemBioChem, pp. S1-S18 (2006).
Wang et al., "A thermostable azo-linker for reversible photoregulation of DNA replication," Tetrahedron Letters 49(34):5087-9 (2008).
Wang et al., "Relative stabilities of triple helices composed of combinations of DNA, RNA and 2'-O-methyl-RNA backbones: chimeric circular oligonucleotides as probes," Nucleic Acids Res. 23(7):1157-64 (1995).
Wu et al., "Reversible stability switching of a hairpin DNA via a photo-responsive linker unit," Chem Commun (Camb). 14(14):1915-7 (2009).
Yamana et al., "Synthesis of oligonucleotides containing a new azobenzene fragment with efficient photoisomerizability," Bioorg Med Chem. 7(12):2977-83 (1999).
Office Action for Canadian Application No. 2,752,543, dated Feb. 27, 2018 (4 pages).

(56) References Cited

OTHER PUBLICATIONS

English Translation of Office Action for Israeli Application No. 214399, dated Mar. 20, 2018 (2 pages).
Notice of Reasons for Rejection for Japanese Application No. 2017-161747, dated Oct. 25, 2018 (11 pages).
Chen et al., "Template-directed chemical ligation to obtain 3'-3' and 5'-5' phosphodiester DNA linkages," Sci Rep. 4:4595 (2014) (6 pages).
Luebke et al., "Nonenymatic ligation of double-helical DNA by alternate-strand triple helix formation," Nucleic Acids Res. 20(12):3005-9 (1992).
Ding, Jinfeng et al., "Gene analysis and Bio-chip technology," Wuhan: Hubei Science and Technology Press, pp. 108-109 (2004) (8 pages).
*Pharmacological frontier-signal, protein factor, gene and modern pharmacology.*. Edited by Wei, Erqing. Beijing: Science Publishing House, pp. 314-316 (1999) (12 pages).
Supplemental Protest and Submission of Prior Art for Canadian Application No. 2,752,543, dated Apr. 24, 2018 (7 pages).
Third-Party Submission of Information for Japanese Application No. 2017-161747, dated Apr. 19, 2018 (198 pages).
Notice of Opposition for Indian Application No. 6461/CHENP/2011, Sep. 8, 2011 (80 pages).
Asanuma et al. "Synthesis of azobenzene-teathered DNA for Reversible photo-regulation of DNA functions: hybridization and transcription," Protocol. 2(1):203-212 (11 pages).
U.S. Appl. No. 61/531,820, Keefe et al.
U.S. Appl. No. 61/536,929, Keefe et al.
Chapter 5: Crosslinking and Photoactivatable Reagents. *Molecular Probes Handbook: A Guide to Fluorescent Probes and Labeling Technologies*, 11th Edition. ThermoFischer Scientific. (2010) (18 pages).
Clark et al., Supplementary Methods for "Design, synthesis and selection of DNA-encoded small-molecule libraries," Nat Chem Biol. 5(9):647-54 (2009) (57 pages).
Communication of a Notice of Opposition for European Patent Application No. 13816635.0, dated Jan. 10, 2019 (37 Pages).
Communication of a Notice of Opposition to European Patent No. 2396459, dated Feb. 9, 2018 (83 pages).
Communication of Opposition to European Patent No. 2,748,357, dated Jan. 4, 2019 (42 Pages).
Kanaya et al., "Template-Directed Polymerization of Oligoadenylates Using Cyanogen Bromide," Biochemistry. 25(23):7423-30 (1986).
Khakshoor et al., "Chemistry of nucleic acids: impacts in multiple fields," Chem Commun. 47(25):7018-24 (2011).
Kleiner et al., "In Vitro Selection of a DNA-Templated Small-Molecule Library Reveals a Class of Macrocyclic Kinase Inhibitors," J Am Chem Soc. 132(33):11779-11791 (2010).
Kocalka et al., "Rapid and Efficient DNA Strand Cross-Linking by Click Chemistry," Chembiochem. 9(8):1280-5 (2008).
Kore et al., "Efficient synthesis of 3-cyanovinylcarbazole-1'-beta-deoxyriboside-5'-triphosphate: a reversible photo-cross-linking probe," Tetrahedron Lett. 53(31):4012-14 (2012).
Lallana et al., "Reliable and efficient procedures for the conjugation of biomolecules through Huisgen azide-alkyne cycloadditions," Angew Chem Int Ed Engl. 50(38):8794-804 (2011).
Notification of Defects for Israeli Patent Application No. 263625, dated Jul. 9, 2019 (12 pages).
Pujari et al., "Cross-Linked DNA Generated by 'Bis-click' Reactions with Bis-functional Azides: Site Independent Ligation of Oligonucleotides via Nucleobase Alkynyl Chains," J Org Chem. 75(24):8693-6 (2010).
Written Opinion for Singaporean Patent Application No. 2014011381, dated Oct. 22, 2019 (8 pages).
Xiong et al., "Cross-Linked DNA: Site-Selective 'Click' Ligation in Duplexes with Bis-Azides and Stability Changes Caused by Internal Cross-Links," Bioconjug Chem. 23(6):1230-43 (2012).
Xiong et al., "Stepwise 'Click' Chemistry for the Template Independent Construction of a Broad Variety of Cross-Linked Oligonucleotides: Influence of Linker Length, Position, and Linking Number on DNA Duplex Stability," J Org Chem. 76:5584-5597 (2011).
Yoshimura et al., Supporting Information for "Ultrafast Reversible Photocrosslinking Reaction: Toward in Situ DNA Manipulation," Org Lett. (2008) (20 pages).
Statement of Grounds of Appeal for Opposition to European Patent No. 2396459, filed Dec. 31, 2019 (53 pages).
Notice of Reasons for Rejection for Japanese Patent Application No. 2019-082384, dated Jun. 22, 2020 (10 pages).
European Search Report for European Patent Application No. 19208965.4, dated Mar. 30, 2020 (10 pages).
Examination Report for Singaporean Application No. 2014011381, dated Apr. 3, 2020 (6 pages).
Ferris et al., "N-cyanoimidazole and diimidazole imine: water-soluble condensing agents for the formation of the phosphodiester bond," Nucleosides Nucleotides. 8(3):407-14 (1989).
Interlocutory Decision in Opposition Proceedings (Art. 101 (3)(a) and 106(2) EPC) for European Application No. 13816635.0, dated Apr. 7, 2020 (144 pages).
Letter from the Opponent in Response to the Summons to Attend Oral Proceedings Pursuant to Rule 115(1) EPC for European Patent No. 2748357, dated Apr. 30, 2020 (7 pages).
Notice of Preliminary Rejection for Korean Patent Application No. 10-2020-7007550, dated May 20, 2020 (9 pages).
Zhao et al., "Effects of 2'-O-methyl nucleotide on ligation capability of T4 DNA ligase," Acta Biochim Biophys Sin (Shanghai). 46(9):727-37 (2014).
Office Action for Chinese Patent Application No. 201711269685X, dated Jul. 27, 2020 (22 pages).
Office Action for Brazilian Patent Application No. PI1008429-0, dated Nov. 24, 2020 (6 pages).
Office Action for Canadian Patent Application No. 2,752,543, dated Oct. 16, 2020 (4 pages).
Office Action for Chinese Application No. 2017/11269685X, dated Feb. 26, 2021 (7 pages).
Notice of Reasons for Rejection and English Translation for Japanese Patent Application No. 2019-082384, dated May 31, 2021 (4 pages).
U.S. Appl. No. 61/152,508.
Bain et al., "Regioselective ligation of oligoribonucleotides using DNA splints," Nucleic Acids Res. 20(16):4372 (1992).
Barrio et al., "Synthesis of Modified Nucleoside 3'-5'-Bisphosphates and Their Incorporation into Oligoribonucleotides with T4 RNA Ligase," Biochemistry. 17(11):2077-2081 (1978) (5 pages).
Bullard et al., "Direct comparison of nick-joining activity of the nucleic acid ligases from bacteriophage T4," Biochem J. 398(1):135-144 (2006) (10 pages).
Communication of a Notice of Opposition to European Patent No. 3211126, dated Jul. 27, 2021 (88 pages).
England et al., "Enzymatic Oligoribonucleotide Synthesis with T4 RNA Ligase," Biochemistry. 17(11):2069-76 (1978) (8 pages).
Iuodka et al., "Study of the substrate specificity of T4 RNA ligase: Interaction of the enzyme with ATP analogs modified through the ribose residue and with affinity sorbents," Biokhimiia. 60(3):478-484 (1995) (7 pages).
Ma et al., "PEG 400, a Hydrophilic Molecular Probe for Measuring Intestinal Permeability," Gastroenterology. 98(1):39-46 (1990) (8 pages).
Nichols et al., "RNA Ligases," Curr Protoc Mol Biol. 3(15):1-4 (2008) (4 pages).
Stark et al., "An RNA ligase-mediated method for efficient creation of large, synthetic RNAs," RNA. 12(11):2014-2019 (2006) (6 pages).
Yamana et al. Nucleosides & Nucleotides, (1998) vol. 17 (1-3), 233-242, published in 1998.†
Ren et al. Angew Chem Int Ed Engl. (1996) vol. 35, No. 7, 743-746, published in 1996.†
Bonora et al., Bioconjugate Chem. (1997) vol. 8, pp. 793-797, published in 1997.†
Jäschke et al. Nucleic Acids Research (1994) vol. 22, No. 22, 4810-4817, published in 1994.†

(56) References Cited

OTHER PUBLICATIONS

Clark et al., Nature Chemical Biology (2009) vol. 5, No. 9,647-654 and Supp. Info. pp. 1-57, published online Aug. 2, 2009.†
Beaucageand Iyer, Tetrahedron (1993), vol. 49, No. 10, pp. 1925-1963, published in 1993.†
Cui, Life (2009), vol. 61, No. 8, pp. 860-863, published in Aug. 2009.†
Abe et al. Nucleic Acids Symposium (2006) Series No. 50, 25-26, published in 2006.†

† cited by third party

Mode 2

- Small molecule tethered to ss or dsDNA
  – DNA could be hairpin on opposite end
- Linkers should vary in size and makeup (typically PEG-like, 20 to 200 atoms)
- Identifier region can be any size, but 5 nt - 20 nt preferred
- Identifier region only codes for A or B and in some schemes, S

FIG. 13A Ligation of DNA Tags

| HP | A | B | C | 3' end |
|---|---|---|---|---|
| T T CTC TCG CCTC AGC CA GGA CC-3'<br>H2N-T GAG AGC GGAG TCG GT CCT (p)-5'<br>T T | 5'-(p)GGAGGACT GT 3'<br>3' GG CCTCCTGA (p) 5' | 5'-(p)CAGACGAC GA 3'<br>3' CA GTCTGCTG(p)-5' | 5'(p)CGATGCTC TT 3'<br>3'CT GCTA CGAG (p)-5' | 5'- (p) GCT GTG CAG GTA GAG TGC-3'<br>3'-AA CGA CAC GTC CAT CTC ACG-5' |

M 1 2 3 4

M 1 2 3

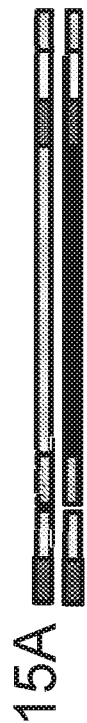
FIG. 15A
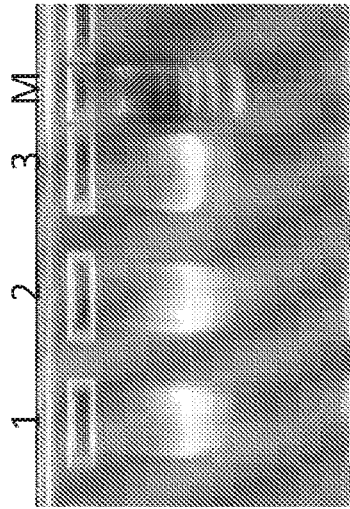
FIG. 15C
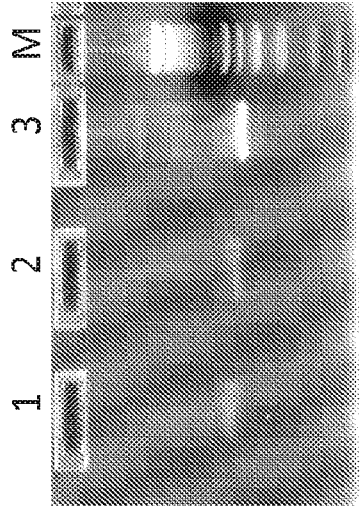
FIG. 15B

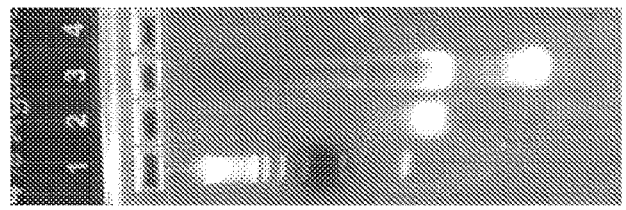
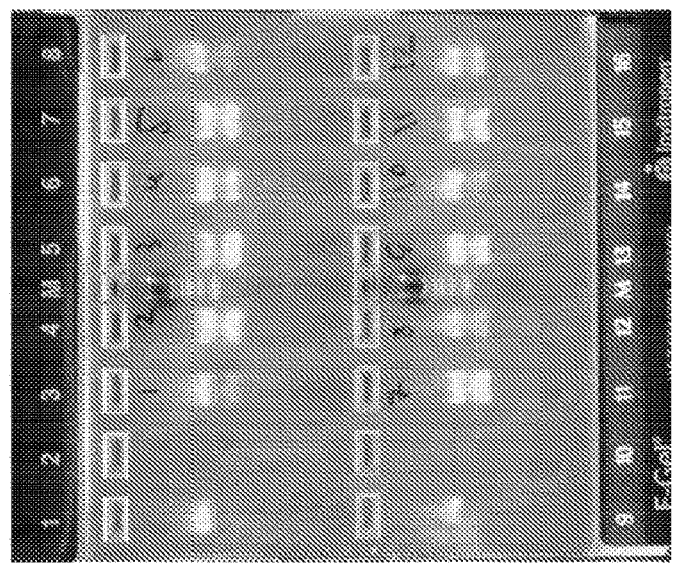
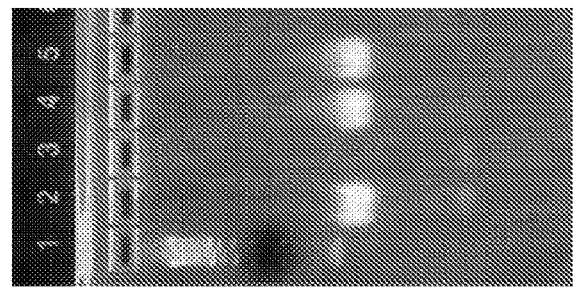

METHODS OF CREATING AND SCREENING DNA-ENCODED LIBRARIES

BACKGROUND OF THE INVENTION

The burgeoning cost of drug discovery has led to the ongoing search for new methods of screening greater chemical space as inexpensively as possible to find molecules with greater potency and little to no toxicity. Combinatorial chemistry approaches in the 1980s were originally heralded as being methods to transcend the drug discovery paradigm, but largely failed due to insufficient library sizes and inadequate methods of deconvolution. Recently, the use of DNA-displayed combinatorial libraries of small molecules has created a new paradigm shift for the screening of therapeutic lead compounds.

Morgan et al. (U.S. Patent Application Publication No. 2007/0224607, hereby incorporated by reference) identifies the major challenges in the use of DNA-displayed combinatorial approaches in drug discovery: (1) the synthesis of libraries of sufficient complexity and (2) the identification of molecules that are active in the screens used. In addition, Morgan et al. states that the greater the degree of complexity of a library, i.e., the number of distinct structures present in the library, the greater the probability that the library contains molecules with the activity of interest. Thus, the chemistry employed in library synthesis must be capable of producing vast numbers of compounds within a reasonable time frame. This approach has been generally successful at identifying molecules with diverse chemotypes and high affinity. However, a number of issues have surfaced with respect to generating libraries of enormous complexity and evaluating the sequencing output on the scale that has been described. For example, purification of a library following multiple chemical transformations (e.g., usually 3 or 4 steps) and biological transformations (e.g., enzymatic ligation of DNA tags) is cumbersome and results in a significant amount of "noise" in the library due either to incomplete synthesis of molecules or to mis-tagging during the ligation step. Furthermore, the amount of sequencing that is required to interrogate selected populations is striking, usually requiring "nextgeneration" sequencing methods. The latter is due to the fact that sophisticated genetic tagging schemes embedded in the DNA portion of the library, together with bioinformatics algorithms for analyzing the "nextgeneration" sequencing output, are required to sift through the noise and identify hits in the library. As a result, even with these methodologies, the sequencing is still not advanced enough to fully capture the diversity of sequences (representing both real hits and "noise") from a given screen.

DNA display of combinatorial small molecule libraries relies on multistep, split-and-pool synthesis of the library, coupled to enzymatic addition of DNA tags that encode both the synthetic step and building block used. Several (e.g., 3 or 4) synthetic steps are typically carried out and encoded, and these include diversity positions (described herein as A, B, and C (FIG. 1)), such as those formed by coupling building blocks with, e.g., amine or carboxylate functional groups onto a chemical scaffold that displays the attached building blocks in defined orientations. One example of a scaffold (S) that is often used in combinatorial libraries is a triazine moiety, which can be orthogonally derivatized in three positions about its ring structure.

The process of library formation can be time consuming, products are often inefficiently purified, and the result is that unknown reactions may occur that create unwanted and/or unknown molecules attached to the DNA. Furthermore, incomplete purification of the library can result in tags cross-contaminating during the ligation steps, resulting in mis-tagging. The end result for screening and sequencing hits from the library is that massively parallel sequencing has to be employed due the inherent "noise" of both DNAs that are attached to molecules that are unintended (e.g., unreacted or side products) or that are mis-tagged. Thus, the efficiency of sequencing is lost.

In some instances, an initiator oligonucleotide, from which the small molecule library is built, contains a primer-binding region for polymerase amplification (e.g., PCR) in the form of a covalently-closed, double-stranded oligonucleotide. This construct is very problematic for performing polymerase reactions, owing to the difficulty of melting the duplex and allowing a primer oligonucleotide to bind and initiate polymerization, which results in an inefficient reaction, reducing yield by 10- to 1000-fold or more.

There exists a need for a more step-wise approach to screening and identifying small molecules that have greater potency and little to no toxicity.

SUMMARY OF THE INVENTION

The present invention features a method for creating and screening simplified DNA-encoded libraries, owing to fewer synthetic steps (e.g., no enzymatic ligation or no covalently closed initiator double-stranded oligonucleotides) and, therefore, substantially less "noise" during the analysis of the encoded oligomers (herein termed "identifier regions"). Thus, sequencing becomes much more efficient, or alternatively, microarray analysis becomes possible, taking into account the inherent biases that can confound interpretation of the data that can be introduced by amplification of the encoding region. We also have identified methods for creating a greater diversity of chemical reactions rather than those simply limited to aqueous conditions to render the DNA-encoded library more hydrophobic and soluble in organic solvents for subsequent steps of library synthesis. In this manner, chemical reactions can be carried out with potentially higher yield, a greater diversity of building blocks, and improved fidelity of the chemical reactions.

Accordingly, the present invention features a method of tagging DNA-encoded chemical libraries by binding a first functional group of a bifunctional linker to an initiator oligonucleotide at the 5' end of the initiator oligonucleotide, wherein the initiator oligonucleotide forms a hairpin structure, and binding a second functional group of the bifunctional linker to a component of the chemical library. The initiator oligonucleotide may include a first identifier region and a second identifier region, such that the second identifier region hybridizes to the first identifier region of the initiator oligonucleotide. The second identifier region may include a fluorescent tag (e.g., a fluorophore or GFP) or biotin label. In addition, the second identifier region is not amplified prior to analysis following a selection step.

In another embodiment, the invention features a method of creating DNA-encoded libraries by (a) creating a first diversity node, (b) encoding the first diversity node in separate vessels, (c) pooling the first diversity node, and (d) splitting the pooled first diversity node into a second set of separate vessels, wherein the first diversity node reacts to form a second diversity node. In certain embodiments, the second diversity node is not encoded and pooled.

In another embodiment, the present invention features a method for creating libraries using semi- or non-aqueous (e.g., organic) chemical reactions with higher yield, a greater diversity of building blocks, and a greater number of chemical reactions that can be used to create more DNA-tagged combinatorial libraries than previously achieved.

In general, the methods of the present invention provide a set of libraries containing, e.g., one or two diversity positions on a chemical scaffold that can be efficiently generated at high yield, screened to identify preferred individual building blocks or combinations of building blocks that reside at the, e.g., one or two diversity positions, and iteratively diversified at, e.g., a second, third, and/or fourth diversity position to create molecules with improved properties. In addition, the methods described herein allow for an expansive and extensive analysis of the selected compounds having a desired biological property, which, in turn, allows for related compounds with familial structural relationships to be identified (e.g., structure-activity relationships).

By "scaffold" is meant a chemical moiety which displays diversity node(s) in a particular special geometry. Diversity node(s) are typically attached to the scaffold during library synthesis, but in some cases one diversity node can be attached to the scaffold prior to library synthesis (e.g., addition of identifier regions). In some embodiments, the scaffold is derivatized such that it can be orthogonally deprotected during library synthesis and subsequently reacted with different diversity nodes (e.g., using identifier tagging at each step).

By "identifier region" is meant the DNA tag portion of the library that encodes the building block addition to the library.

By "initiator oligonucleotide" is meant the starting oligonucleotide for library synthesis which also contains a covalently attached linker and functional moiety for addition of a diversity node or scaffold. The oligonucleotide can be single- or double-stranded. The oligonucleotide can consist of natural or modified bases.

By "functional moiety" is meant a chemical moiety comprising one or more building blocks that can be selected from any small molecule or designed and built based on desired characteristics of, for example, solubility, availability of hydrogen bond donors and acceptors, rotational degrees of freedom of the bonds, positive charge, negative charge, and the like. The functional moiety must be compatible with chemical modification such that it reacts with the headpiece. In certain embodiments, the functional moiety can be reacted further as a bifunctional or trifunctional (or greater) entity. Functional moieties can also include building blocks that are used at any of the diversity nodes or positions. Examples of building blocks and encoding DNA tags are found in Tables 1 and 2. See, e.g., U.S. Patent Application Publication No. 2007/0224607, hereby incorporated by reference.

By "building block" is meant a chemical structural unit which is linked to other chemical structural units or can be linked to other such units. When the functional moiety is polymeric or oligomeric, the building blocks are the monomeric units of the polymer or oligomer. Building blocks can also include a scaffold structure (e.g., a scaffold building block) to which is, or can be, attached one or more additional structures (e.g., peripheral building blocks). The building blocks can be any chemical compounds which are complementary (i.e., the building blocks must be able to react together to form a structure comprising two or more building blocks). Typically, all of the building blocks used will have at least two reactive groups, although some of the building blocks used will have only one reactive group each. Reactive groups on two different building blocks should be complementary, i.e., capable of reacting together to form a covalent bond.

By "linker" is meant a molecule that links the nucleic acid portion of the library to the functional displayed species. Such linkers are known in the art, and those that can be used during library synthesis include, but are not limited to, 5'-O-Dimethoxytrityl-1',2'-Dideoxyribose-3'-[(2-cyanoethyl)-(N,N-diisopropyl)]-phosphoramidite; 9-O-Dimethoxytrityl-triethylene glycol, 1-[(2-cyanoethyl)-(N,N-diisopropyl)]-phosphoramidite; 3-(4,4'-Dimethoxytrityloxy) propyl-1-[(2-cyanoethyl)-(N,N-diisopropyl)]-phosphoramidite; and 18-O-Dimethoxytritylhexaethyleneglycol, 1-[(2-cyanoethyl)-(N, N-diisopropyl)]-phosphoramidite. Such linkers can be added in tandem to one another in different combinations to generate linkers of different desired lengths. By "branched linker" is meant a molecule that links the nucleic acid position of the library to 2 or more identical, functional species of the library. Branched linkers are well known in the art and examples can consist of symmetric or asymmetric doublers (1) and (2) or a symmetric trebler (3). See, for example, Newcome et al., Dendritic Molecules: Concepts, Synthesis, Perspectives, VCH Publishers (1996); Boussif et al., *Proc. Natl. Acad. Sci. USA* 92: 7297-7301 (1995); and Jansen et al., *Science* 266: 1226 (1994).

As used herein, the term "oligonucleotide" refers to a polymer of nucleotides. The oligonucleotide may include DNA or any derivative thereof known in the art that can be synthesized and used for base-pair recognition. The oligonucleotide does not have to have contiguous bases, but can be interspersed with linker moieties. The oligonucleotide polymer may include natural nucleosides (e.g., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), and/or modified phosphate groups (e.g., phosphorothioates and 5'-N-phosphoramidite linkages).

By "operatively linked" is meant that two chemical structures are linked together in such a way as to remain linked through the various manipulations they are expected to undergo. Typically, the functional moiety and the encoding oligonucleotide are linked covalently via an appropriate linking group. For example, the linking group may be a bifunctional moiety with a site of attachment for the encoding oligonucleotide and a site of attachment for the functional moiety.

By "small molecule" is meant a molecule that has a molecular weight below about 1000 Daltons. Small molecules may be organic or inorganic, and may be isolated from, e.g., compound libraries or natural sources, or may be obtained by derivatization of known compounds.

Other features and advantages of the invention will be apparent from the following detailed description, the drawings, the examples, and the claims.

BRIEF DESCRIPTION OF THE DRAWINGS

FIG. 13A is a scheme of the ligation of the DNA tags.

FIG. 14A is a gel showing synthesis and purification steps. Samples were mixed with loading buffer and boiled. M: marker; Lane 1: HP-1+ DTAF; Lanes 2 and 2a: HP-1-DTAF+biotin (two independent reactions); Lanes 3-6 (steps of purification/model selection using streptavidin Dynal beads): Lane 3: flow-through; Lane 4: last wash (washed with water at 80° C. for 10 minutes); Lanes 5 and 5': elution with 25 mM EDTA at 90° C. ($1^{st}$ and $2^{nd}$); Lanes 6 and 6': elution with 25 mM EDTA and 5 mM NaOH at 90° C. ($1^{st}$ and $2^{nd}$). FIG. 14B is a gel showing binding of HP-1-DTAF-biotin ("library of 1") to streptavidin. Samples were mixed with gel loading buffer and directly loaded onto the gel without boiling. Samples, as in the gel of FIG. 14A, were incubated with an excess of streptavidin in 50 mM NaCl/10 mM Tris HCl, pH 7.0, for 10 minutes. "S" indicates the addition of streptavidin. Samples 5 and 6 were pooled together. Lane 1: HP-1-DTAF; Lane 1S: HP-1-DTAF+streptavidin; Lane 2: HP-1-DTAF-biotin (desalted); Lane 2S: HP-1-DTAF-biotin+streptavidin; Lane 4: last wash (washed with water at 80° C. for 10 minutes); Lane 4S: last wash sample+streptavidin; Lane 5+6: pooled samples 5, 5', 6 and 6' (elution fractions from streptavidin beads, purified and selected HP-1-DTAF-biotin; Lane 5+6S': purified and selected HP-1-DTAF-biotin+streptavidin. Note that there is no noticeable difference in migration between different the steps of "library of 1" synthesis. FIG. 14C is a 4% agarose gel of headpiece (Trilink) HP-T, reacted with DTAF. Lane 1: Marker; Lane 2: DTAF; Lane 3 HP-T-DTAF. Left panel: UV visualization of the gel (ethidium bromide staining); Right panel: same gel scanned for fluorescence at excitation wavelength 450 nm (green, fluorescein). FIG. 14D is a 4-12% SDS NuPage gel with MES running buffer, showing binding of HP-T-DTAF-biotin to streptavidin. Samples were mixed with gel loading buffer and directly loaded onto the gel without boiling. Samples, as in the gel of FIG. 14A, were incubated with an excess of streptavidin in 50 mM NaCl/10 mM Tris HCl, pH 7.0, for 10 minutes. Lane 1: DTAF; Lane 2: HP-T-DTAF; Lane 3: HP-T-DTAF+streptavidin; Lane 4: HP-T-DTAF-biotin (desalted); Lane 5: HP-T-DTAF-biotin+streptavidin; Lane 6: pooled samples 5, 5', 6 and 6' (elution fractions from streptavidin beads, purified and selected HP-1-DTAF-biotin; Lane 7: purified and selected HP-1-DTAF-biotin+streptavidin.

FIG. 15A is a scheme of the synthesis of the construct for the T7 RNAP intracellular delivery experiment. The VH dsDNA clone was PCR amplified to append a BsmI site at the 5' end upstream of the T7 promoter. Following restriction digestion and purification, the construct was ligated to HP-1-DTAF-R7 (headpiece modified with DTAF and (-Arg-εAhx)$_6$-Arg peptide). FIG. 15B is an electrophoretic gel of the ligation reaction. Lanes 1 and 2 show different HP-1 samples ligated to VH; Lane 3 shows unligated VH PCR product; and M is the marker. FIG. 15C is an electrophoretic gel showing validation for T7 promoter activity. The gel shows a T7 Megascript (Ambion, Inc.) reaction using samples from Lanes 1-3 of FIG. 15B.

FIGS. 16A-C are agarose gel electrophoresis of the steps in library 10×10 synthesis FIG. 16A is a 4% agarose gel of headpiece (Trilink) HP-T ligated with tag A. Lane 1: Marker; Lane 2: HP-T; Lane 3: Tag A annealed; Lane 4: HP-T ligated with tag A; Lane 5: HP-T ligated with tag A and desalted on Zeba column. FIG. 16B is a 2% agarose gel of HP-T-A ligation with 12 different tags B. Lane M: Marker, Lanes 1 and 9: HP-T-A; Lanes 3, 4, 5, 6, 7, 8, 11, 12, 13, 14, 15 and 16: HP-T-A ligation with tags B1-B12. FIG. 16C is a 4% agarose gel of the pooled library (library B), with tags A and B1-B12 ligated, after reaction with cyanouric chloride and amines B1-B12. Lane 1: Marker; Lane 2: HP-T-A; Lane 3: Library-B pooled and desalted on Zeba columns.

DETAILED DESCRIPTION OF THE INVENTION

Figure 1:
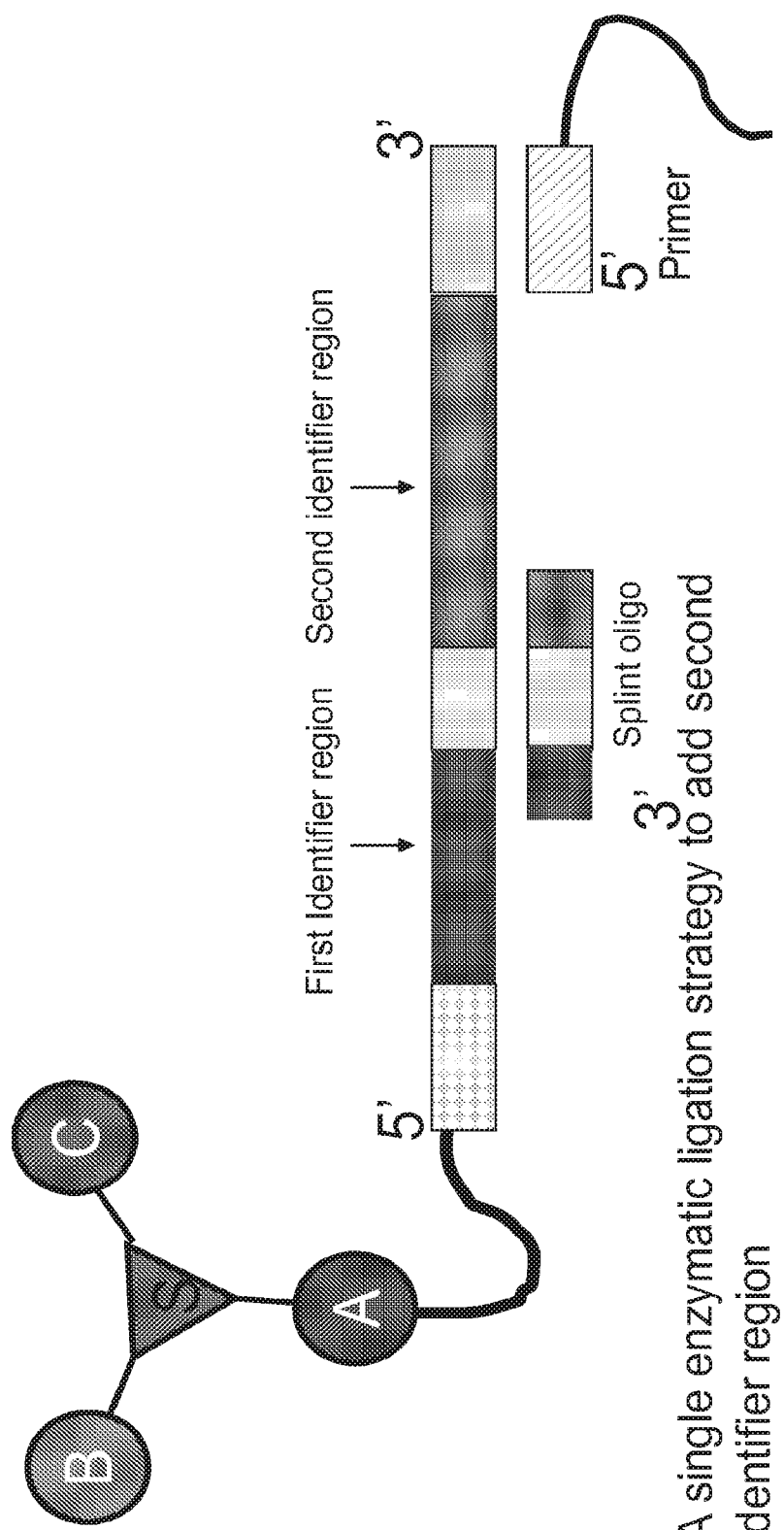
FIG. 1 is a schematic illustrating the diversity positions A, B, and C.

The present invention features a number of methods for identifying one or more compounds that bind to a biological target. The methods include synthesizing a library of compounds, wherein the compounds contain a functional moiety having one or more diversity positions. The functional moiety of the compounds is operatively linked to an initiator oligonucleotide that identifies the structure of the functional moiety. In summary, Mode 1 provides a number of methods to preserve the double-stranded character of the dsDNA during library synthesis, which is important during the chemical reaction step, and can be used (as shown in FIGS. 2-6) for generating up to two diversity nodes. Mode 2 (FIGS. 7-9) anticipates one node of diversity and uses a hairpin oligonucleotide that is covalently closed (e.g., via a hairpin or chemically) on the distal end to the linker. Mode 3 provides methods to create libraries with one, two, three, or more nodes of diversity. Modes 1, 2, and 3 are described in detail below.

Mode 1

The present invention features a method for identifying one or more compounds that bind to a biological target. The method includes synthesizing a library of compounds, wherein the compounds contain a functional moiety having no greater than two diversity positions. The functional moiety of the compounds is operatively linked to an initiator oligonucleotide that identifies the structure of the functional moiety by providing a solution containing A initiator compounds.

The initiator oligonucleotide includes a linker L (e.g., polyethylene glycol) with an integer of one or greater, wherein the initiator oligonucleotides contain a functional moiety that includes A building blocks attached to L and separated into A reaction vessels, wherein A is an integer of two or greater, which is operatively linked to an initiator oligonucleotide that identifies the A building blocks.

In some embodiments, the A building blocks can be further derivatized through a common node S. In other embodiments, A is subsequently transformed with S, S being a scaffold molecule that allows further nodes of diversity introduction. In some embodiments, A-S can be screened directly, representing a single node of diversity. In other embodiments, the A-S reaction vessels (e.g., which may first include a purification of A-S from starting materials) are mixed together and aliquoted into B reaction vessels, wherein B is an integer of one or greater, and reacted with one of B building blocks. A-S-B, still in B reaction vessels, is in some cases reacted with a C building block, where C is an integer of one, is purified, and subjected to a polymerization or ligation reaction using B primers, in which the B primers differ in sequence and identify the B building blocks.

In certain embodiments, A-S can be an integer of one. In one embodiment, A-S can be linked directly to B initiator oligonucleotides, and following reaction of B building blocks, the B reactions are mixed. In certain embodiments, the A-S-B mixture, where B represents the only diversity node, is screened directly, representing a single node of diversity. In other embodiments, the A-S-B mixture, where B represents the only diversity node, is subsequently aliquoted into C reaction vessels, reacted with C building blocks, and subjected to second strand polymerization or ligation reaction using C primers, in which the C primers differ in sequence and identify the C building blocks.

In certain embodiments, B can be an integer of one and A-S is greater than one, in which case A-S, now derivatized with B, is aliquoted into C reaction vessels, reacted with C building blocks, and subjected to second strand polymerization reaction using C primers, in which the C primers differ in sequence and identify the C building blocks. This general strategy can be expanded to include additional diversity nodes (e.g., D, E, F, etc.) so that the first diversity node is reacted with building blocks and/or S and encoded by an initial oligonucleotide, mixed, re-aliquoted into vessels and then the subsequent diversity node is derivatized by building blocks, which is encoded by the primer used for the polymerization or ligation reaction.

In certain embodiments, A can be an integer of one, B can be an integer of one, and C initiator oligonucleotides are used. A-S-B, attached to C initiator oligonucleotides, is formed in C reaction vessels, reacted with C building blocks, and screened directly.

In certain embodiments, S is reacted first with the initiator oligonucleotide, and A, B and/or C (e.g., or D, E, F, and so on) are subsequently reacted.

In certain embodiments, A, B, or C (e.g., or D, E, F, and so on) can contain sites for additional diversity nodes. If this is the case, then S may or may not be used or needed to introduce additional diversity nodes.

Figure 2:
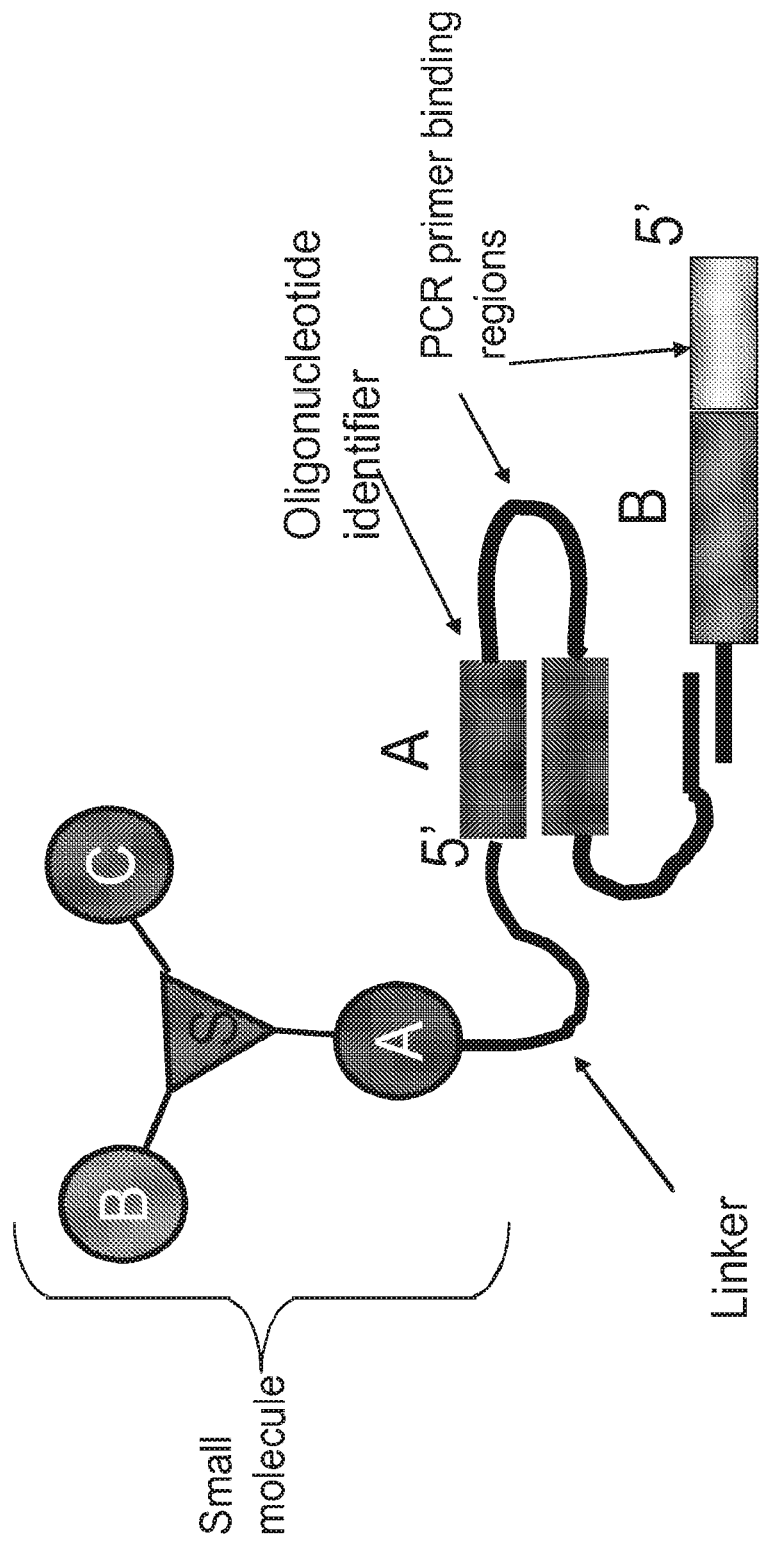
FIG. 2 is a schematic of a DNA-encoded chemical library member of Mode 1, showing, in part, the initiator oligonucleotide, which includes a hairpin structure complementary at the identifier region, which has been reacted with A and B diversity nodes. The identifier region for B is being added. In this figure, the "C" diversity node is the potential position for an additional diversity position to be added following the addition of B identifier region.

In one embodiment, the initiator oligonucleotide includes a hairpin structure complementary at the identifier region (FIG. 2). The identifier region can be, e.g., 2 to 100 base pairs in length, preferably 5 to 20 base pairs in length, and most preferably 6 to 12 base pairs in length. The initiator oligonucleotide further includes a sequence in the loop region of the hairpin structure that can serve as a primer binding region for amplification (FIG. 3), such that the primer binding region has a higher melting temperature for its complementary primer (e.g., which can include flanking identifier regions) than the identifier region alone.

Figure 3:
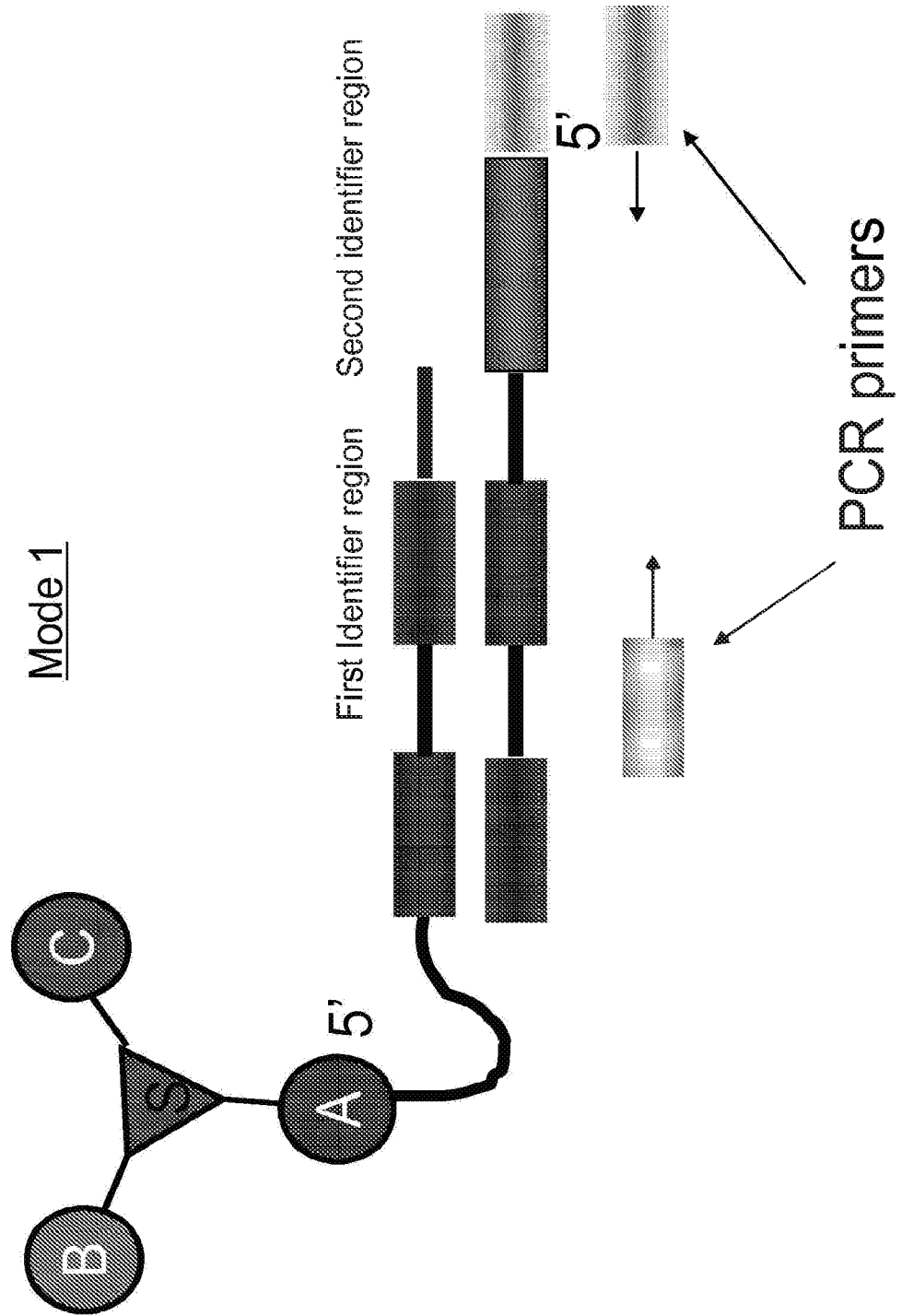
FIG. 3 is a schematic of a DNA-encoded chemical library member of Mode 1, showing, in part, the initiator oligonucleotide, which includes a sequence in the loop region of the hairpin structure that can serve as a primer binding region for amplification.
Figure 4:
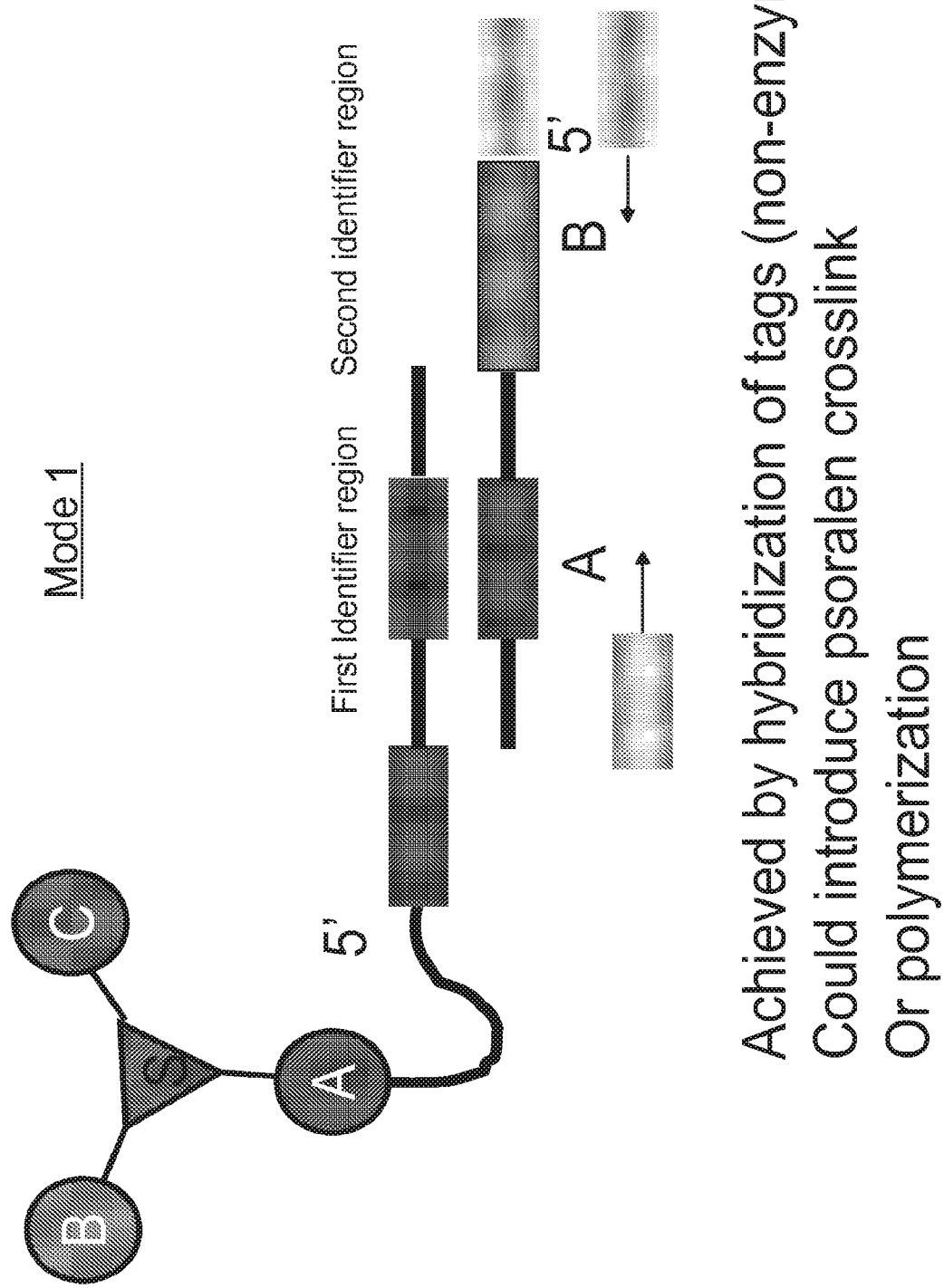
FIG. 4 is a schematic of a DNA-encoded chemical library member of Mode 1, showing, in part, the initiator oligonucleotide, which includes a non-complementary sequence on the 3' end of the molecule that can serve to bind a second identifier region for either polymerization or for enzymatic ligation.

In one embodiment, the loop region may include modified bases that can form higher affinity duplex formations than unmodified bases, such modified bases being known in the art (FIG. 3). The initiator oligonucleotide can further include a non-complementary sequence on the 3' end of the molecule that can serve to bind a second identifier region for either polymerization or for enzymatic ligation (FIG. 4). In one embodiment, the strands can be subsequently cross-linked, e.g., using psoralen.

Figure 5:
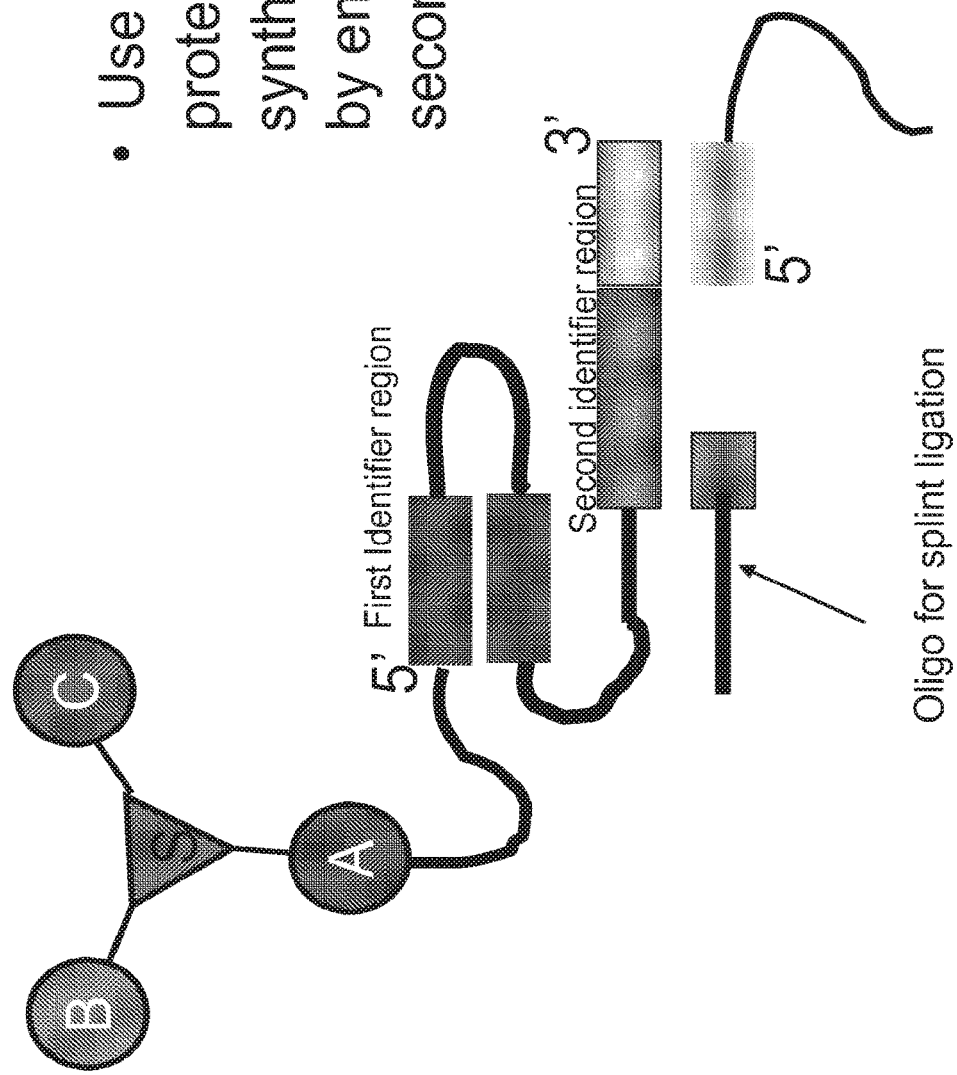
FIG. 5 is a schematic of a DNA-encoded chemical library member of Mode 1, showing, in part, the initiator oligonucleotide, wherein the loop region of the initiator oligonucleotide and at least the identifier region on the 3' side of the loop region can serve to hybridize to a complementary oligonucleotide that also contains a second identifier region.
Figure 6:
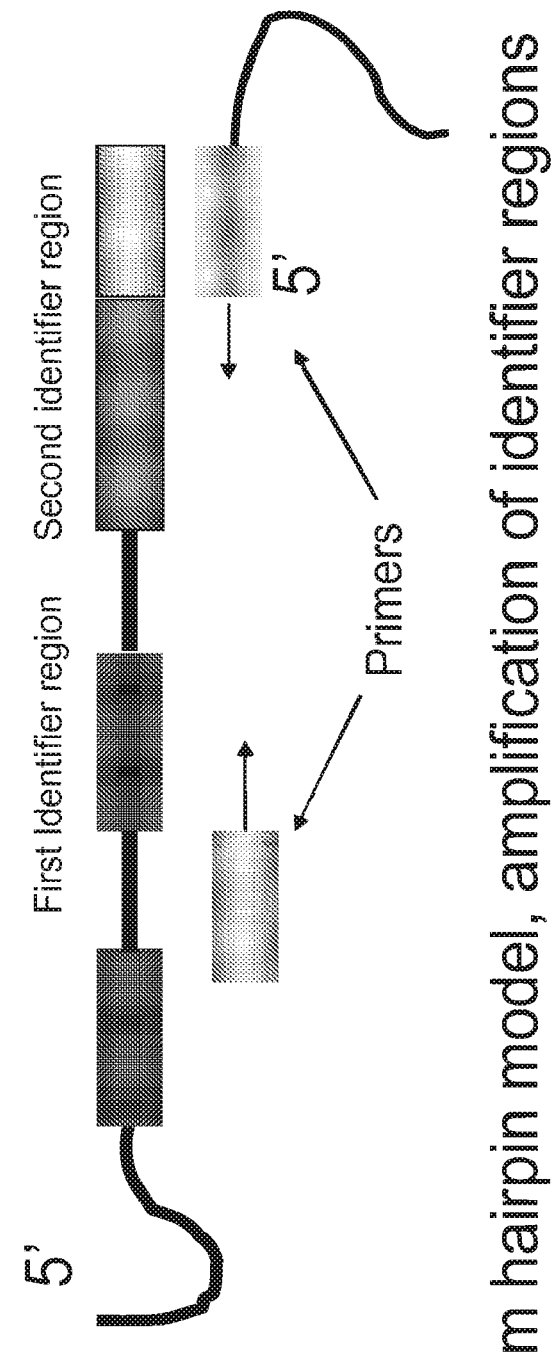
FIG. 6 is a schematic of PCR amplification of the hairpin model, as presented in FIG. 5.
Figure 7:
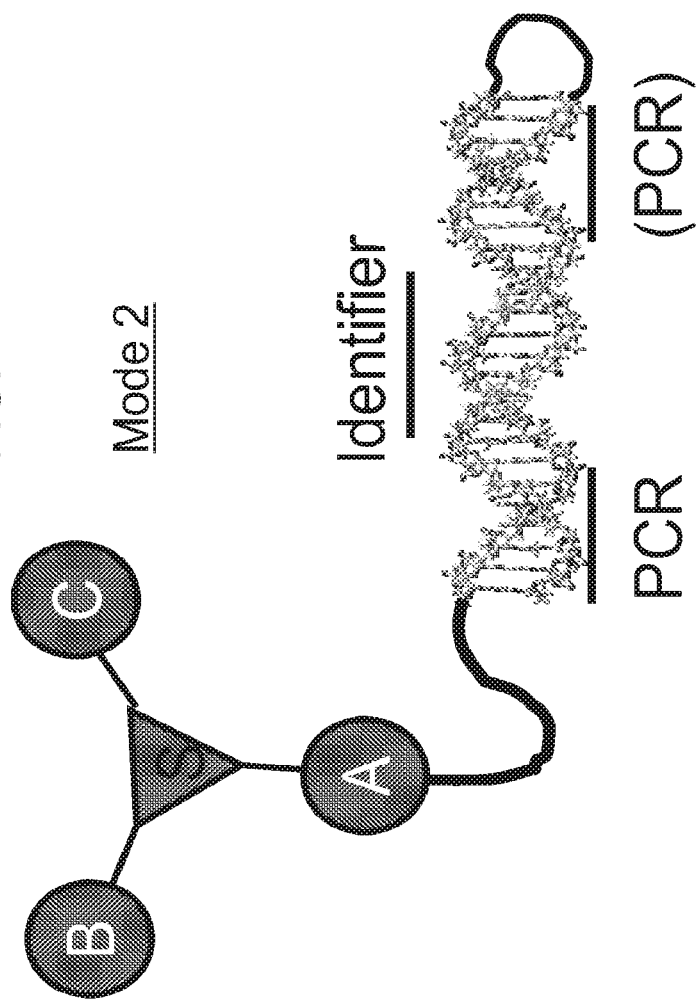
FIG. 7 is a schematic of a DNA-encoded chemical library member of Mode 2, showing a hairpin oligonucleotide that is covalently closed (e.g., via a hairpin or chemically) on the distal end to the linker.

In another embodiment, the loop region and at least the identifier region on the 3' side of the loop region can serve to hybridize to a complementary oligonucleotide that also contains a second identifier region (FIG. 5). In cases where many building blocks and corresponding tags are used (e.g., 100 tags), a mix-and-split strategy may be employed during the oligonucleotide synthesis step to create the necessary number of tags. Such mix-and-split strategies for DNA synthesis are known in the art. In one embodiment, the strands can be subsequently crosslinked, e.g., using psoralen. The resultant library members can be amplified by PCR following selection for binding entities versus a target(s) of interest (FIG. 6).

For example, a headpiece, which includes an initiator oligonucleotide, may be reacted with a linker and A, which includes, for example, 1000 different variants. For each A building block, a DNA tag A may be ligated or primer extended to the headpiece. These reactions may be performed in, e.g., a 1000-well plate or 10×100 well plates. All reactions may be pooled, optionally purified, and split into a second set of plates. Next, the same procedure may be performed with B building blocks, which also include, for example, 1000 different variants. A DNA tag B may be ligated to the headpiece, and all reactions may be pooled. A library of 1000×1000 combinations of A to B (i.e., 1,000,000 compounds), tagged by 1,000,000 different combinations of tags. The same approach may be extended to add variants C, D, E, etc. The generated library may then be used to identify compounds that bind to the target. The composition of the compounds that bind to the library can be assessed by PCR and sequencing of the DNA tags to identify the compounds that were enriched.

Mode 2

Figure 8:
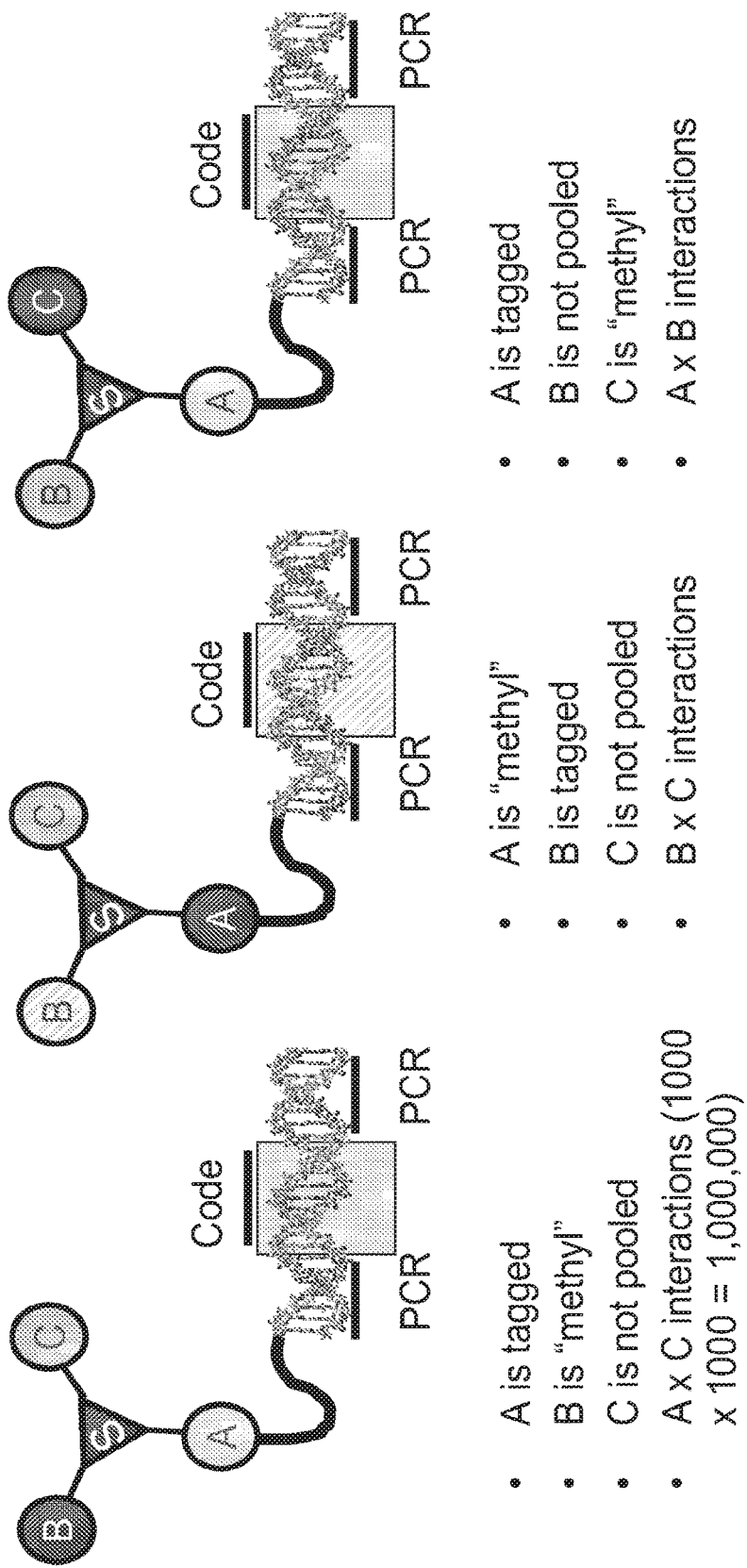
FIG. 8 is a schematic of a DNA-encoded chemical library member of Mode 2, showing the inclusion of additional diversity nodes.

In another embodiment (FIG. 7), the method includes synthesizing a library of compounds, wherein the compounds contain a functional moiety having no greater than two diversity positions. The functional moiety of the compounds is operatively linked to an initiator oligonucleotide, which contains a unique genetic sequence that identifies the structure of the functional moiety by providing a solution comprising A initiator compounds, wherein L is an integer of one or greater, where the initiator compounds include a functional moiety having A building blocks separated into A reaction vessels, where, e.g., A is an integer of two or greater, which is operatively linked to an initial oligonucleotide which identifies the A building blocks. In some embodiments, the A building blocks are pre-derivatized with a common S. In other embodiments, A is subsequently transformed with S, S being a scaffold molecule that allows further nodes of diversity introduction. Next, the A-S reaction vessels (which may first include a purification of A-S from starting materials) are mixed together and aliquoted into B reaction vessels, wherein B is an integer of one or greater, and reacted with one of B building blocks. A-S-B, still in B reaction vessels is, in some embodiments, reacted with a C building block, where C is an integer of one, are purified, and kept separate in B vessels for screening. In some embodiments, A-S is an integer of one. In one embodiment, A-S can be linked directly to B initiator oligonucleotides and, following the reaction of B building blocks, the B reactions are mixed and aliquoted into C reaction vessels, reacted with C building blocks, and kept separate in C vessels for screening. In other embodiments, B can be an integer of one and A-S is greater than one, in which case A-S, now derivatized with B, is aliquoted into C reaction vessels reacted with C building blocks, and kept separate in C vessels for screening. This general strategy can be expanded to include additional diversity nodes (e.g., D, E, F, etc.) so that the first diversity node is reacted with building blocks and/or S and encoded by an initiator oligonucleotide, mixed, re-aliquoted into vessels, and then the subsequent diversity node is derivatized by building blocks and kept in their respective vessels for screening (FIG. 8).

For example, as described in Mode 1, a headpiece, which includes an initiator oligonucleotide, may be reacted with a linker and A building blocks, which include, for example, 1000 different variants. For each A building block, a DNA tag A may be ligated or primer extended to the headpiece. The reactions may be pooled. Next, the same procedure may be performed with B building blocks, but a DNA tag is not added for B. Because B is not coded for, all "B" reactions may be pooled (e.g., 1000 reactions) and a selection step may be performed to identify all A building blocks that produce the desired binding effect with unknown B building blocks. A library of A building blocks identified in the selection step (e.g., 10 A building blocks) may then be reacted with the same 1000 B building blocks, resulting in a screen of 10,000 compounds or less. In this round, DNA tags for B may be added and B building blocks that produce the desired binding effect in combination with the, e.g., 10 A building blocks can be identified, resulting in a step-wise convolution of an initial library of, for example, 1,000,000 compounds. A set of these final compounds may be individually tested to identify the best, e.g., binders, activators, or inhibitors.

To avoid pooling all of the reactions after B synthesis, a BIND Reader (SRU Biosystems), for example, may be used to monitor binding on a sensor surface in high throughput format (e.g., 384 well plates and 1536 well plates). For example, the A building blocks may be encoded with DNA tags and the B building blocks may be position encoded. Binders can then be identified using a BIND sensor, sequencing, and microarray analysis or restriction digest analysis of the A tags. This analysis allows for the identification of combinations of A and B building blocks that produce the desired molecules. Other methods for monitoring binding known to those of skill in the art may be used including, e.g., ELISA.

Modes 1 and 2

The initiator oligonucleotide of Modes 1 and 2 may contain a hairpin structure, complementary at the identifier region. The initiator oligonucleotide further contains a sequence in the loop region of the hairpin structure that can serve as a primer-binding region for amplification, such that the primer binding region has a higher melting temperature for its complementary primer (which can include flanking identifier regions) than the identifier region alone.

In one embodiment, the initiator oligonucleotide includes a linker molecule capable of being functionally reacted with building blocks. The linker molecule can be attached directly to the 5' end of the oligonucleotide through methods known in the art or can be embedded within the molecule, e.g., off of a derivatized base (e.g., the C5 position of uridine), or the linker can be placed in the middle of the oligonucleotide using standard techniques known in the art.

The initiator oligonucleotide may be single-stranded or double-stranded. The formation of a double-stranded oligonucleotide may be achieved through hairpin formation of the oligonucleotide or through cross-linking using, e.g., a psoralen moiety, as known in the art.

The initiator oligonucleotide may contain two primer-binding regions (e.g., to enable a PCR reaction) on either side of the identifier region that encodes the building block. Alternatively, the initiator oligonucleotide may contain one primer-binding site on the 5' end. In other embodiments, the initiator oligonucleotide is a hairpin, and the loop region forms a primer-binding site or the primer-binding site is introduced through hybridization of an oligonucleotide to the identifier region on the 3' side of the loop. A primer oligonucleotide, containing a region homologous to the 3' end of the initiator oligonucleotide and carrying a primer binding region on its 5' end (e.g., to enable a PCR reaction) may be hybridized to the initiator oligonucleotide, and may contain an identifier region that encodes the building blocks used at one of the diversity positions. The primer oligonucleotide may contain additional information, such as a region of randomized nucleotides, e.g., 2 to 16 nucleotides in length, which is included for bioinformatic analysis.

In one embodiment, the initiator oligonucleotide does not contain a PCR primer-binding site.

In another embodiment, the library of compounds, or a portion thereof, is contacted with a biological target under conditions suitable for at least one member of the library of compounds to bind to the target, followed by removal of library members that do not bind to the target, and analyzing the identifier region or regions. Exemplary biological targets include, e.g., enzymes (e.g., kinases, phosphatases, methylases, demethylases, proteases, and DNA repair enzymes), proteins involved in protein:protein interactions (e.g., ligands for receptors), receptor targets (e.g., GPCRs and RTKs), ion channels, bacteria, viruses, parasites, DNA, RNA, prions, or carbohydrates).

In one embodiment, the library of compounds, or a portion thereof, is contacted with a biological target under conditions suitable for at least one member of the library of compounds to bind to the target, followed by removal of library members that do not bind to the target, followed by amplification of the identifier region by methods known in the art, and subsequently analyzing the identifier region or regions by methods known in the art.

In one embodiment the method of amplification of the identifier region can include, e.g., polymerase chain reaction (PCR), linear chain amplification (LCR), rolling circle amplification (RCA), or any other method known in the art to amplify nucleic acid sequences.

In a further embodiment, the library of compounds is not pooled following the final step of building block addition and the pools are screened individually to identify compound(s) that bind to a target.

Figure 9:
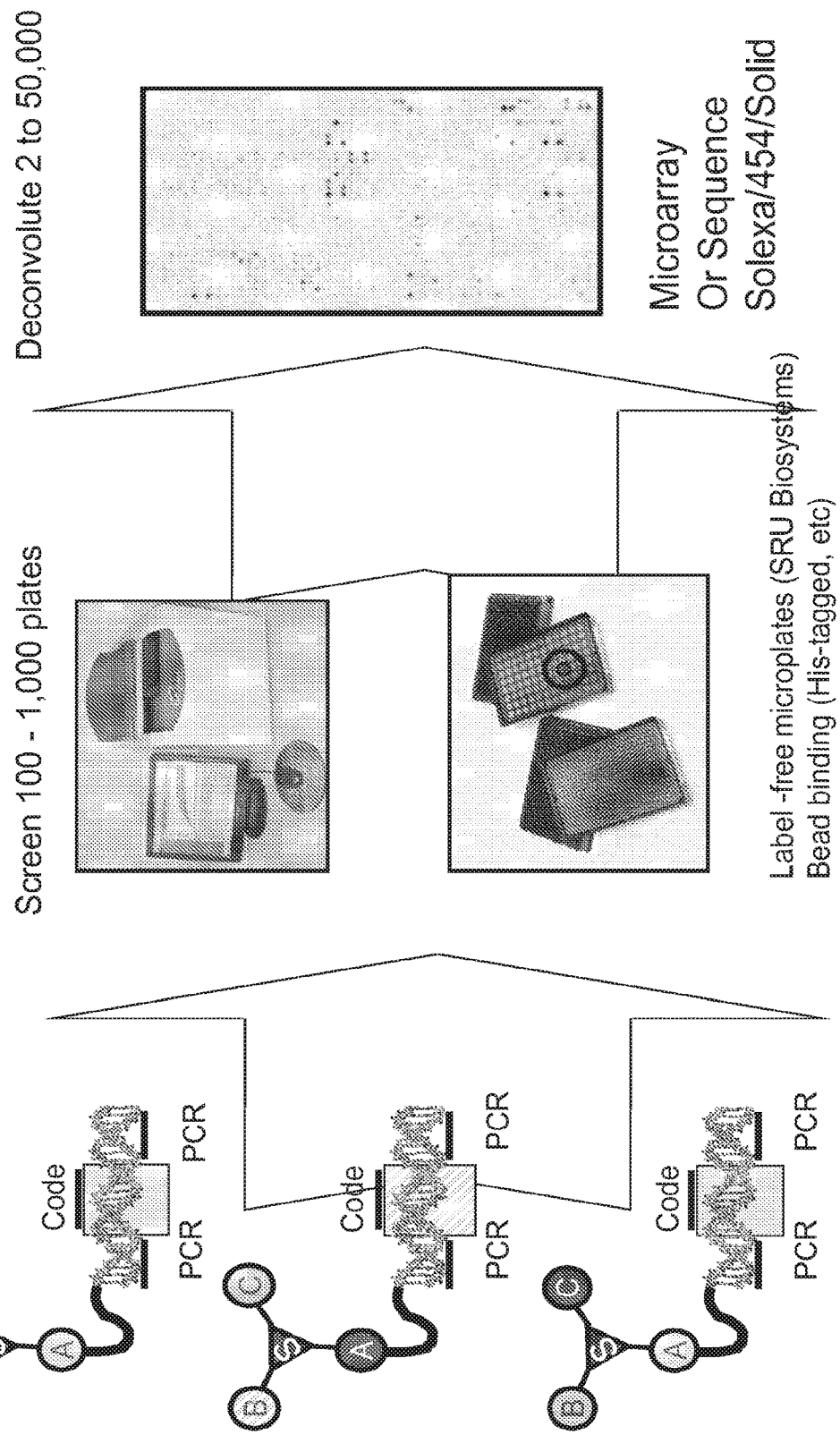
FIG. 9 is a schematic of a DNA-encoded chemical library member of Mode 2, showing the steps for screening of libraries and methods for deconvoluting the identifier regions.

In another embodiment, the molecules that bind to a target are not subjected to amplification, but are analyzed directly. Methods of analysis include, e.g., microarray analysis or bead-based methods for deconvoluting the identifier regions (FIG. 9). Molecules that bind during the screening step may also be detected by a label-free photonic crystal biosensor.

In one embodiment, the initiator oligonucleotide and/or the primer oligonucleotide contain a functional moiety that allows for its detection by, e.g., fluorescent tags, Q dots, or biotin.

In one embodiment, the microarray analysis uses advanced detection capability, such as, e.g., evanescent resonance photonic crystals.

In one embodiment, the method of amplifying includes forming a water-in-oil emulsion to create a plurality of aqueous microreactors, wherein at least one of the microreactors has at least one member of a library of compounds that binds to the target, a single bead capable of binding to the encoding oligonucleotide of the at least one member of the library of compounds that binds to the target, and amplification reaction solution containing reagents necessary to perform nucleic acid amplification, amplifying the encoding oligonucleotide in the microreactors to form amplified copies of the encoding oligonucleotide, and binding the amplified copies of the encoding oligonucleotide to the beads in the microreactors.

Once the building blocks from the first library that bind to the target of interest have been identified, a second library may be prepared in an iterative fashion, in which one or two additional nodes of diversity are added, and the library is created and diversity sampled as described herein. This process can be repeated as many times as necessary to create molecules with desired molecular and pharmaceutical properties.

Exemplary A building blocks include, e.g., amino acids (not limited to alpha-amino acids), click-chemistry reactants (e.g., azide or alkine chains) with an amine, or a thiol reactant. The choice of A building block depends on, for example, the nature of the reactive group used in the linker, the nature of a scaffold moiety, and the solvent used for the chemical synthesis. See, e.g., Table 1.

TABLE 1

Exemplary Position A Building Blocks

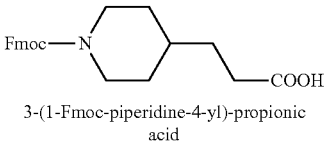
3-(1-Fmoc-piperidine-4-yl)-propionic acid

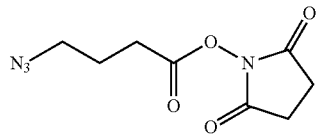
4-Azido-butan-1-oic acid N-Hydroxysuccinimide Ester

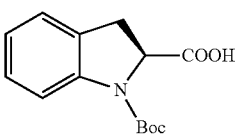
Boc-L-indoline-2-carboxylic acid

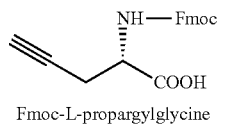
Fmoc-L-propargylglycine

TABLE 1-continued

Exemplary Position A Building Blocks

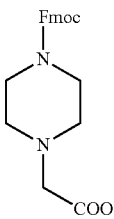

Fmoc-(4-carboxymethyl)piperazine

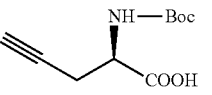

Boc-D-propargylglycine·DCHA

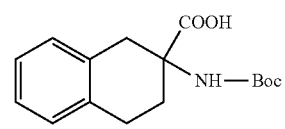

Boc-2-amino-1,2,3,4-tetrahydro-naphthalene-2-carboxylic acid

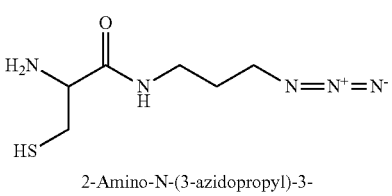

2-Amino-N-(3-azidopropyl)-3-mercaptopropionamide

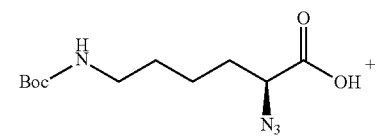

(S)-(−)-2-Azido-6-(Boc-amino)hexanoic acid

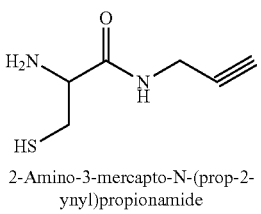

2-Amino-3-mercapto-N-(prop-2-ynyl)propionamide

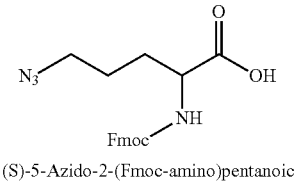

(S)-5-Azido-2-(Fmoc-amino)pentanoic acid

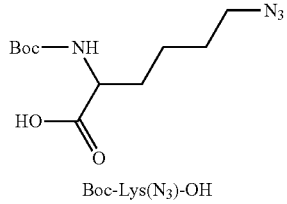 [SMILES: CC(C)(C)OC(=O)NC(CCCCN=[N+]=[N-])C(=O)O]

Boc-Lys(N$_3$)-OH

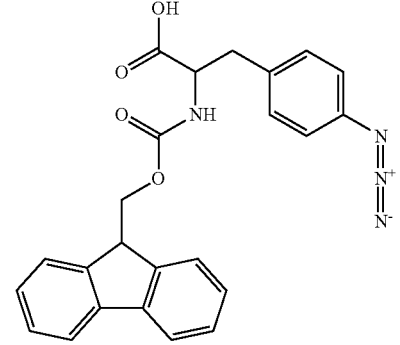

Fmoc-4-azidophenylalanine

Exemplary B and C building blocks are described in Tables 2 and 3, respectively. A restriction site may be introduced, for example, in the B or C position for analysis of the final product and selection by performing PCR and restriction digest with one of the corresponding restriction enzymes.

TABLE 2

Examples of Position B Building Blocks and Encoding DNA Tags

| Chemical Name and Structure | Restriction Site (Restriction Enzyme) | Top Strand Bottom Strand |
|---|---|---|
| 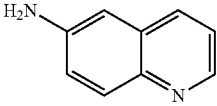<br>6-Aminoquinoline (B1) | T/CCGGA (BspEI) | 5'-Phos-CCTCCGGAGA (SEQ ID NO: 1)<br>5'-Phos-TCCGGAGGAC (SEQ ID NO: 2) |
| 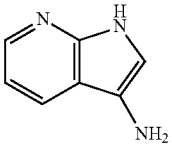<br>3-Amino-7-azaindole, 1H-pyrrolo[2,3-b]pyridin-3-ylamine (B2) | GGC/GCC (SfoI) | 5'-Phos-CCGGCGCCGA (SEQ ID NO: 3)<br>5'-Phos-GGCGCCGGAC (SEQ ID NO: 4) |
| 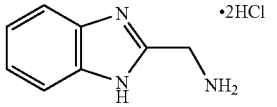<br>2-(Aminomethyl) benzimidazole dihydrochloride (B3) | GGTAC/C (KpnI) | 5'-Phos-CCGGTACCGA (SEQ ID NO: 5)<br>5'-Phos-GGTACCGGAC (SEQ ID NO: 6) |
| 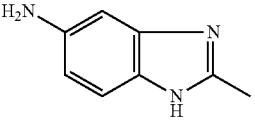<br>2-Methyl-1H-benzimidazol-5-amine (B4) | CAC/GTG (PmlI) | 5'-Phos-CCCACGTGGA (SEQ ID NO: 7)<br>5'-Phos-CACGTGGGAC (SEQ ID NO: 8) |
| 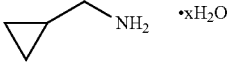<br>(Aminomethyl)cyclopropane (B5) | GAGCT/C (SacI) | 5'-Phos-CCGAGCTCGA (SEQ ID NO: 9)<br>5'-Phos-GAGCTCGGAC (SEQ ID NO: 10) |
| <br>3-Aminophthalimide (B6) | G/GATCC (BamHI) | 5'-Phos-CCGGATCCGA (SEQ ID NO: 11)<br>5'-Phos-GGATCCGGAC (SEQ ID NO: 12) |
| 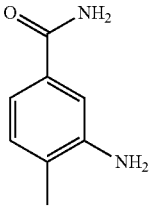<br>3-Amino-4-methylbenzamide (B7) | AT/CGAT (BspDI) | 5'-Phos-CCATCGATGA (SEQ ID NO: 13)<br>5'-Phos-ATCGATGGAC (SEQ ID NO: 14) |
| 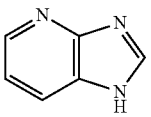<br>4-Azabenzimidazole (B8) | A/AGCTT (HindIII) | 5'-Phos-CCAAGCTTGA (SEQ ID NO: 15)<br>5'-Phos-AAGCTTGGAC (SEQ ID NO: 16) |

TABLE 2-continued

Examples of Position B Building Blocks and Encoding DNA Tags

| Chemical Name and Structure | Restriction Site (Restriction Enzyme) | Top Strand Bottom Strand |
|---|---|---|
| 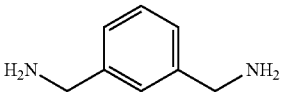 m-Xylylenediamine (B9) | A/GATCT (BglII) | 5'-Phos-CCAGATCTGA (SEQ ID NO: 17) 5'-Phos-AGATCTGGAC (SEQ ID NO: 18) |
| 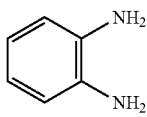 1,2-Phenylenediamine (B10) | G/AATTC (EcoRI) | 5'-Phos-CCGAATTCGA (SEQ ID NO: 19) 5'-Phos-GAATTCGGAC (SEQ ID NO: 20) |
| 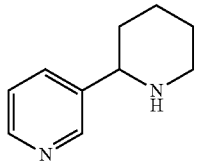 Anabasine (B11) | T/GATCA (BclI) | 5'-Phos-CCTGATCAGA (SEQ ID NO: 21) 5'-Phos-TGATCAGGAC (SEQ ID NO: 22) |
| 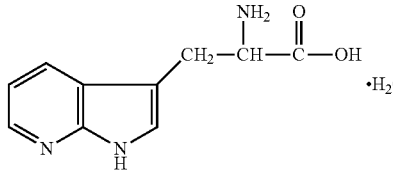 DL-7-Azatryptophan hydrate (B12) | CA/TATG (NdeI) | 5'-Phos-CCCATATGGA (SEQ ID NO: 23) 5'-Phos-CATATGGGAC (SEQ ID NO: 24) |

TABLE 3

Examples of Position C Building Blocks and Encoding DNA Tags

| Chemical Name and Structure | Top Strand Bottom Strand |
|---|---|
| 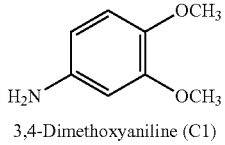 3,4-Dimethoxyaniline (C1) | 5'-Phos-GAACCTGCTT (SEQ ID NO: 25) 5'-Phos-GCAGGTTCTC (SEQ ID NO: 26) |
| 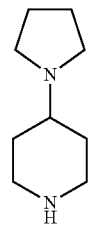 4-(1-Pyrrolidinyl)piperidine (C2) | 5'-Phos-GAAGACGCTT (SEQ ID NO: 27) 5'-Phos-GCGTCTTCTC (SEQ ID NO: 28) |
| 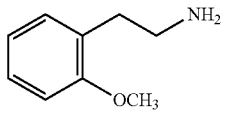 2-Methoxyphenethylamine (C3) | 5'-Phos-GACCAGACTT (SEQ ID NO: 29) 5'-Phos-GTCTGGTCTC (SEQ ID NO: 30) |

TABLE 3-continued

Examples of Position C Building Blocks and Encoding DNA Tags

| Chemical Name and Structure | Top Strand Bottom Strand |
|---|---|
| 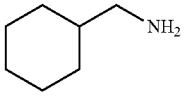 Cyclohexanemethylamine (C4) | 5'-Phos-GACGACTCTT (SEQ ID NO: 31) 5'-Phos-GAGTCGTCTC (SEQ ID NO: 32) |
| 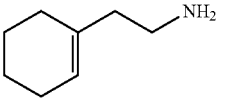 2-(1-Cyclohexenyl)ethylamine (C5) | 5'-Phos-GACGCTTCTT (SEQ ID NO: 33) 5'-Phos-GAAGCGTCTC (SEQ ID NO: 34) |
| 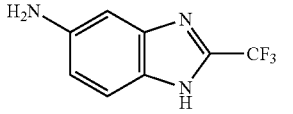 5-Amino-2-(trifluoromethyl) benzimidazole (C6) | 5'-Phos-GAGCAACCTT (SEQ ID NO: 35) 5'-Phos-GGTTGCTCTC (SEQ ID NO: 36) |

TABLE 3-continued

Examples of Position C Building Blocks and Encoding DNA Tags

| Chemical Name and Structure | Top Strand / Bottom Strand |
|---|---|
| 5-Fluoro-3-(4-piperidinyl)-1,2-benzisoxazole hydrochloride (C7) | 5'-Phos-GAGCCATCTT (SEQ ID NO: 37) <br> 5'-Phos-GATGGCTCTC (SEQ ID NO: 38) |
| Isobutylamine (C8) | 5'-Phos-GCAACCACTT (SEQ ID NO: 39) <br> 5'-Phos-GTGGTTGCTC (SEQ ID NO: 40) |
| 4-Fluorobenzylamine (C9) | 5'-Phos-GCACAGACTT (SEQ ID NO: 41) <br> 5'-Phos-GTCTGTGCTC (SEQ ID NO: 42) |
| 5-(Aminomethyl)indole (C10) | 5'-Phos-GCGATCACTT (SEQ ID NO: 43) <br> 5'-Phos-GTGATCGCTC (SEQ ID NO: 44) |
| 2-[(2-chloro-6-fluorobenzyl)thio]ethylamine (C11) | 5'-Phos-GCGGTTACTT (SEQ ID NO: 45) <br> 5'-Phos-GTAACCGCTC (SEQ ID NO: 46) |
| 1-(4-Methylphenyl)piperazine (C12) | 5'-Phos-GCATGACCTT (SEQ ID NO: 47) <br> 5'-Phos-GGTCATGCTC (SEQ ID NO: 48) |
| N,N-Dimethyl-N'-ethylethylenediamine (C13) | 5'-Phos-GCGTACTCTT (SEQ ID NO: 49) <br> 5'-Phos-GAGTACGCTC (SEQ ID NO: 50) |

Mode 3

In either of the modes described herein (e.g., Modes 1 and 2), the headpiece oligonucleotide may be modified to support solubility in semi- or non-aqueous (e.g., organic) conditions. The headpiece, in certain embodiments, includes the identifier region. In other embodiments, the headpiece with linker can first be derivatized with a building block (e.g., a functional moiety) or scaffold, and the identifier sequence is then added.

Nucleotide bases of the headpiece can be rendered more hydrophobic by modifying, for example, the C5 positions of T or C bases with aliphatic chains without significantly disrupting their ability to hydrogen bond to their complementary bases. See, e.g., Table 4 for examples of modified bases. In addition, the headpiece oligonucleotide can be interspersed with modifications that promote solubility in organic solvents. For example, azobenzene phosphoramidite can introduce a hydrophobic moiety into the headpiece design. Such insertions of hydrophobic amidites into the headpiece can occur anywhere in the molecule. However, the insertion cannot interfere with subsequent tagging using additional DNA tags during the library synthesis or ensuing PCR reactions once a selection is complete or microarray analysis, if used for tag deconvolution. Such additions to the headpiece design described herein would render the headpiece soluble in, for example, 15%, 25%, 30%, 50%, 75%, 90%, 95%, 98%, 99%, or 100% organic solvent. Thus, addition of hydrophobic residues into the headpiece design allows for improved solubility in semi- or non-aqueous (e.g., organic) conditions, while rendering the headpiece competent for nucleic acid tagging. Furthermore, DNA tags that are subsequently introduced into the library can also be modified at the C5 position of T or C bases such that they also render the library more hydrophobic and soluble in organic solvents for subsequent steps of library synthesis.

TABLE 4

Exemplary modified nucleotide bases

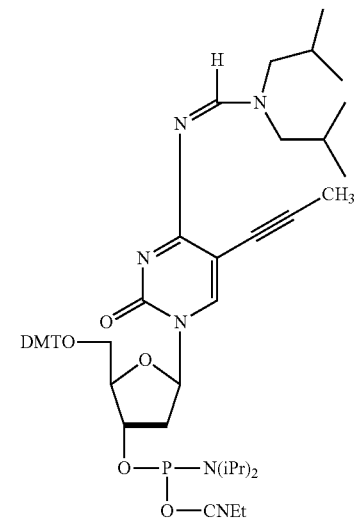

5'-Dimethoxytrityl-N4-
diisobutylaminomethylidene-5-(1-
Propynyl)-
2'-deoxyCytidine,3'-[(2-cyanoethyl)-(N,N-
diisopropyl)]-phosphoramidite

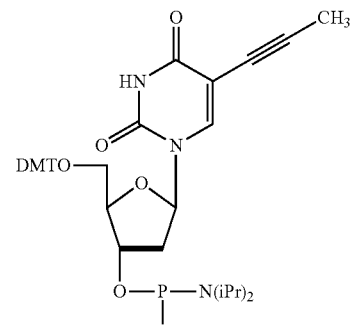

5'-Dimethoxytrityl-5-(1-Propynyl)-2'-
deoxyUridine,3'-[(2-cyanoethyl)-
(N,N-diisopropyl)]-phosphoramidite

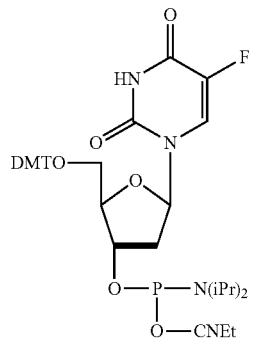

5'-Dimethoxytrityl-5-fluoro-2'-
deoxyUridine,3'-[(2-cyanoethyl)-
(N,N-diisopropyl)]-phosphoramidite

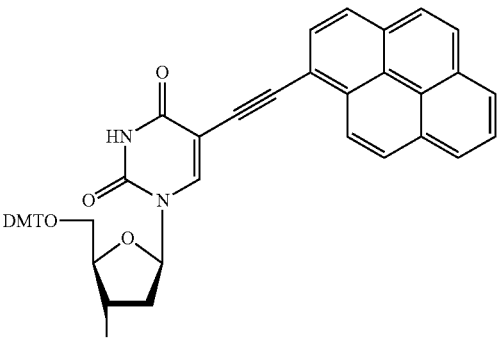

5'-Dimethoxytrityl-5-(pyren-1-yl-ethynyl)-
2'-deoxyUridine,
3'-[(2-cyanoethyl)-(N,N-diisopropyl)]-
phosphoramidite The linker molecule between the headpiece and small molecule library can be varied to increase the solubility of the headpiece in organic solvent. A wide variety of linkers are commercially available that can couple the headpiece with the small molecule library. Linkers are empirically selected for a given small molecule library design (scaffolds and building blocks) such that the library can be synthesized in organic solvent, for example, 15%, 25%, 30%, 50%, 75%, 90%, 95%, 98%, 99%, or 100% organic solvent. The linker can be varied using model reactions prior to library synthesis to select the appropriate chain length that solubilizes the headpiece in organic solvent. Such linkers may include linkers with, e.g., increased alkyl chain length, increased polyethylene glycol units, branched species with positive charges (to neutralize the negative phosphate charges on the headpiece), or increased amounts of hydrophobicity (for example, addition of benzene ring structures).

The linker molecule may provide an appropriate spacer between the headpiece DNA and member of a chemical library. For example, bifunctional linkers may be used. In certain embodiments, bifunctional linkers may include, for example, three parts. Part 1 may be a reactive group, which forms a covalent bond with DNA, such as, e.g., a carboxylic acid, preferably activated by a N-hydroxy succinimide (NHS) ester to react with an amino group on the DNA (e.g., amino-modified dT), an amidite to modify the 5' or 3' end of a single-stranded DNA headpiece (achieved by means of standard oligonucleotide chemistry), click chemistry pairs (azide alkyne cycloaddition in the presence of Cu(I) catalyst), or thiol reactive groups. Part 2 may also be a reactive group, which forms a covalent bond with the chemical library, either a building block in the position A or scaffold moiety. Such a reactive group could be, e.g., an amine, a thiol, an azide, or an alkyne for water based reactions or multiple other reactive groups for the organic-based reactions. Part 3 may be a chemically inert spacer of variable length, introduced between Part 1 and 2. Such a spacer can be a chain of ethylene glycol units (e.g., PEGs of different lengths), an alkane, an alkene, polyene chain, or peptide chain. The linker can contain branches or inserts with hydrophobic moieties (such as, e.g., benzene rings) to improve solubility of the headpiece in organic solvents, as well as fluorescent moieties (e.g. fluorescein or Cy-3) used for library detection purposes.

Examples of commercially available linkers include, e.g., amino-carboxylic linkers (e.g., peptides (e.g., Z-Gly-Gly-Gly-Osu or Z-Gly-Gly-Gly-Gly-Gly-Gly-Osu), PEG (e.g., Fmoc-aminoPEG2000-NHS or amino-PEG (12-24)-NHS), or alkane acid chains (e.g., Boc-ε-aminocaproic acid-Osu)), click chemistry linkers (e.g., peptides (e.g., azidohomalanine-Gly-Gly-Gly-OSu or propargylglycine-Gly-Gly-Gly-OSu), PEG (e.g., azido-PEG-NHS), or alkane acid chains (e.g., 5-azidopentanoic acid, (S)-2-(azidomethyl)-1-Boc-pyrrolidine, or 4-azido-butan-1-oic acid N-hydroxysuccinimide ester)), thiol-reactive linkers (e.g., PEG (e.g., SM(PEG)n NHS-PEG-maleimide), alkane chains (e.g., 3-(pyridin-2-yldisulfanyl)-propionic acid-Osu or sulfosuccinimidyl 6-(3'-[2-pyridyldithio]-propionamido)hexanoate))), amidites for oligonucleotide synthesis (e.g., amino modifiers (e.g., 6-(trifluoroacetylamino)-hexyl-(2-cyanoethyl)-(N,N-diisopropyl)-phosphoramidite), thiol modifiers (e.g., S-trityl-6-mercaptohexyl-1-[(2-cyanoethyl)-(N,N-diisopropyl)]-phosphoramidite, or chick chemistry modifiers (e.g., 6-hexyn-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)).

Hydrophobic residues in the headpiece design may be varied with the linker design to facilitate library synthesis in organic solvents. For example, the headpiece and linker combination is designed to have appropriate residues wherein the octanol:water coefficient (Poct) is from, e.g., 1.0 to 2.5.

EXAMPLES

The following examples are intended to illustrate the invention. They are not meant to limit the invention in any way.

Example 1

Preparation of the Headpiece (Variant 1)

A phosphorylated oligonucleotide headpiece (oligo HP) having the following sequence was synthesized and HPLC purified by IDT DNA.

```
                                    (SEQ ID NO: 51)
5'-(phosphate)TCCTGGCTGAGGCGAGAGTT(dT-C6-NH)

TTCTCTCGCCTCAGCCAGGACC-3'
```

Figure 10:
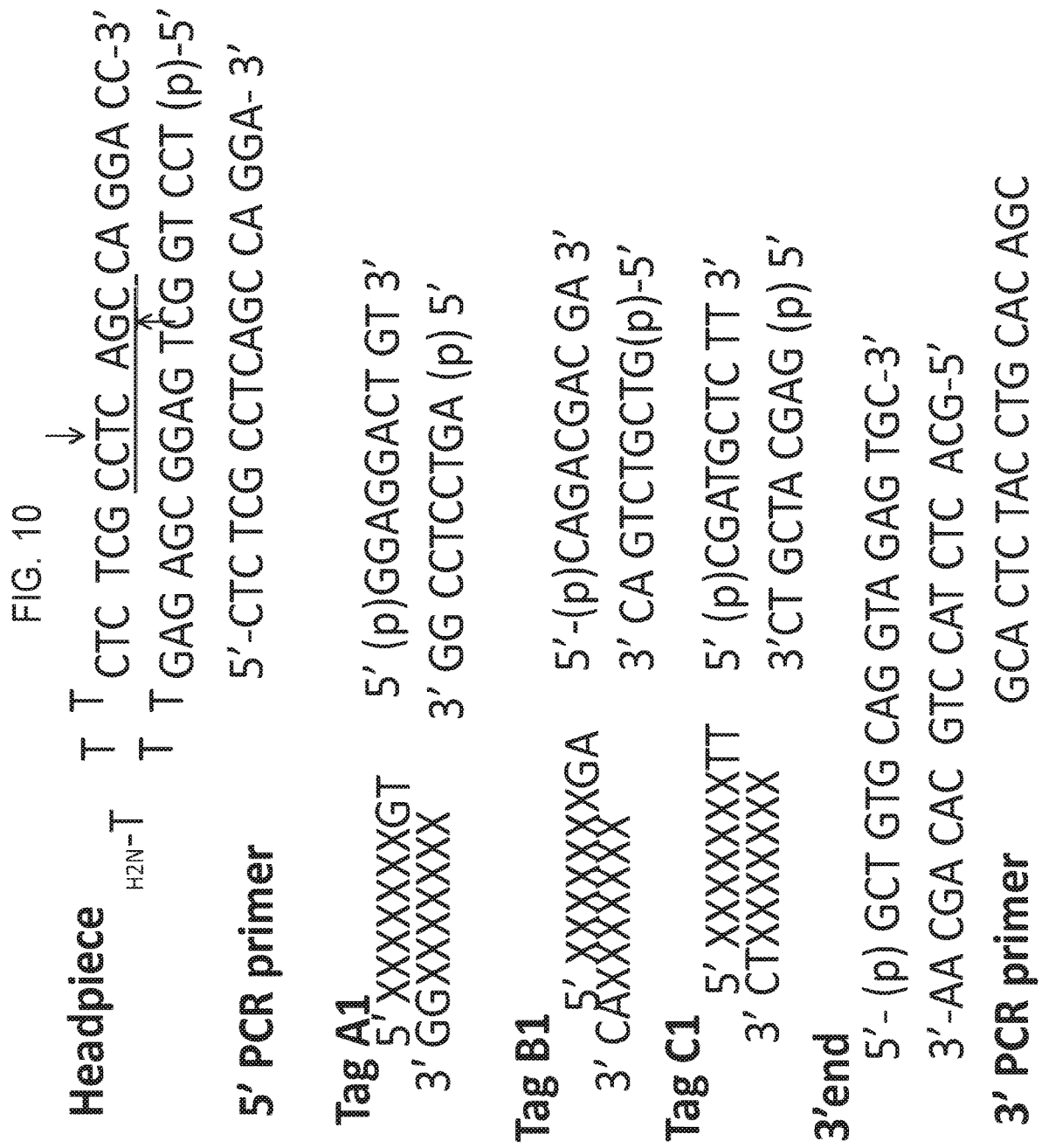
FIG. 10 is a schematic showing oligonucleotides used in library synthesis. Headpiece (HP) was synthesized by IDT DNA and HPLC purified. Arrows indicate the site for BbvCI restriction (underlined) or Nb.BbvCI or Nt.BbvCI nicking digest. Sequences of the DNA tags A1, B1, and C1 (top and bottom strands), the 5' and 3' PCR primers, and the 3' end of the HP are also shown.

The oligonucleotide folds into a hairpin (FIG. 10) with an overhang and contains a cleavage site (CCTCAGC) for restriction enzyme BbvCI or nicking versions of this enzyme Nb.BbvCI or Nt.BbvCI, which can cleave either the top or bottom strand (New England BioLabs). In the middle of the hairpin loop, the side chain C5-amino-modified dT is inserted (dT-C6-NH; "C6" refers to a carbon 6 linker), which was used for the coupling of the amino-PEG linker (PEG2000, approximately 45 ethylene glycol units). The top and bottom strands of the DNA tags A, B, and C were synthesized and purified by IDT DNA and purified by standard desalting. Longer oligonucleotides, such as the 3' end and PCR primers, were synthesized by IDT DNA and HPLC purified.

Ten nanomoles of the oligo HP were dissolved in 50 µl water. A 20-fold molar excess of Fmoc-amino-PEG2000-carboxyl-NHS ester (JenKem Technology USA) was dissolved in 50 µl dimethylformamide (DMF) and was added to the oligonucleotide solution in 2 portions over the course of 2 hours at room temperature (final solvent composition of 50% DMF/50% water). Subsequently, 60 µl of 1 M Tris HCl, pH 7.0 (final concentration of 200 mM), was added to quench the excess of NHS esters, and the solution was incubated for an additional 30 minutes at room temperature. The resulting reaction mixture was diluted to 500 µl with water and was desalted by passing through a NAP-5 column (Sephadex-25, GE Healthcare).

Figure 11:
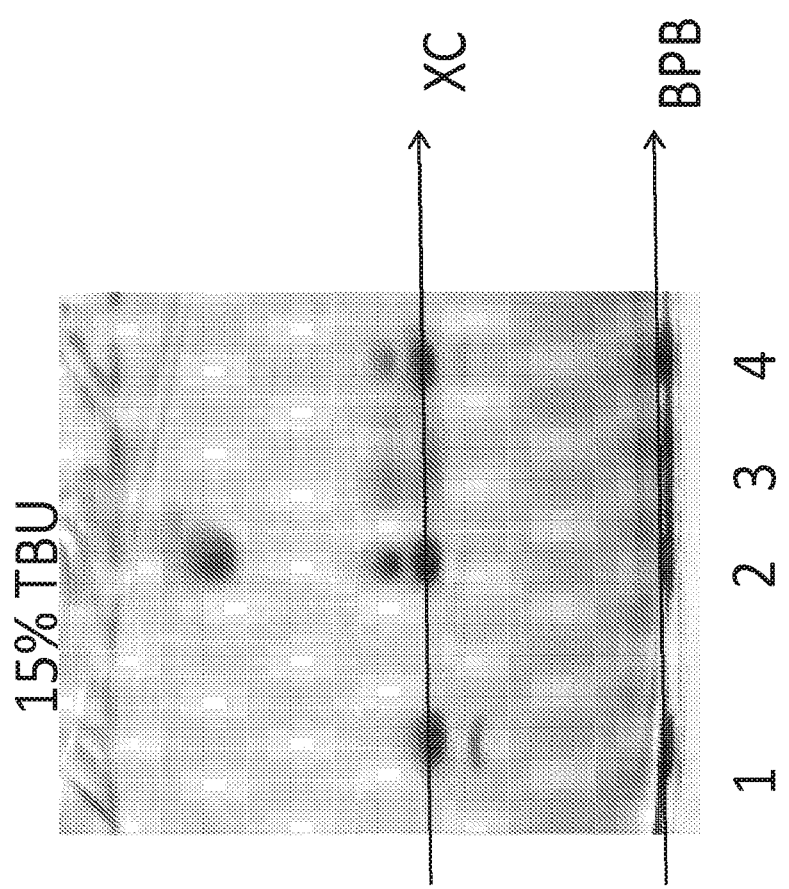
FIG. 11 is an electrophoretic gel (TBE-urea (15%) gel electrophoresis; UV shadowing on a TLC plate) of the headpiece at different steps of its synthesis. Headpiece HP (IDT DNA) was acylated by Fmoc-amino-PEG2000-NHS (JenKem Technology USA). Lane 1 is the HP (IDT DNA) oligonucleotide (42 nts). Lane 2 is HP acylated with Fmoc-amino-PEG2000-NHS. Following Tris-HCl addition, some deprotection of Fmoc is observed. Lane 3 is the crude reaction with piperidine, showing complete deprotection of Fmoc. Lane 4 is the same as Lane 3 after desalting on a NAP-5 column and lyophilization. (XC: xylene cyanol (migrates as 60 nt DNA); BPB: bromophenol blue (migrates as 15 nt DNA)

The resulting material was lyophilized and dissolved in 100 µl water. 20 µl of piperidine (to a final concentration of 20%) was added and incubated for 2 hours at room temperature. A cloudy precipitate was formed due to deprotection of the amine and release of the water insoluble Fmoc group. The reaction was then filtered through 0.2-µm spin-filters (Millipore) and precipitated using 300 mM sodium acetate by the addition of 3 volumes of ethanol. The Fmoc-protected form of the modified oligonucleotide was found to be soluble in ethanol and isopropanol. Due to high coupling efficiency, the resulting headpiece (HP-1) was used without further purification (FIG. 11).

Example 2

Preparation of the Headpiece (Variant 2)

A complete headpiece (HP-1) having the following sequence was prepared by Trilink, Inc., following a similar procedure as described above, and RP-HPLC purified.

```
                                    (SEQ ID NO: 52)
5'-(phosphate)TCCTGGCTGAGGCGAGAGTT(dT-C6-NH)(X)

TTCTCTCGCCTCAGCCAGGACC-3'
``` where X stands for amino-PEG2000.

Example 3

Synthesis of a Model Library Member

Step 1: Coupling of DTAF

In order to prepare a "library of 1," a model compound, 5-(4,6-dichlorotriazinyl-aminofluorescein) (DTAF; Anaspec) (FIG. 12), was coupled to the amino group of HP-1. DTAF structurally represents a trichlorotriazine scaffold with one amino compound coupled. To form a library, trichlorotriazine scaffolds can be derivatized with a diversity of building blocks at each of the three chlorine positions. DTAF also provides a fluorescent label to the model library. The reaction (10 µl) was set up as follows. To 5 µl of 400 µM HP-1 dissolved in water, 2 µl of 750 mM borate buffer, pH 9.5, and 1 µl of DMF were added. DTAF was dissolved in DMF to 50 mM and 2 µl was added to the reaction. Final concentrations of the HP-1 and DTAF were 200 µM and 10 mM, respectively, thus generating a 50-fold excess of DTAF.

The final DMF concentration was 30%. It was noticed that HP-1 stayed soluble in up to 90% DMF, demonstrating that it was soluble in an organic solvent, e.g., DMF. The reaction was allowed to proceed at 4° C. for 16-20 hours. The reaction mixture was then diluted with water to 30-50 μl and desalted on a Zeba spin column (Pierce). No further purification was completed at this point.

Step 2: Coupling of Amino-Biotin

Figure 12:
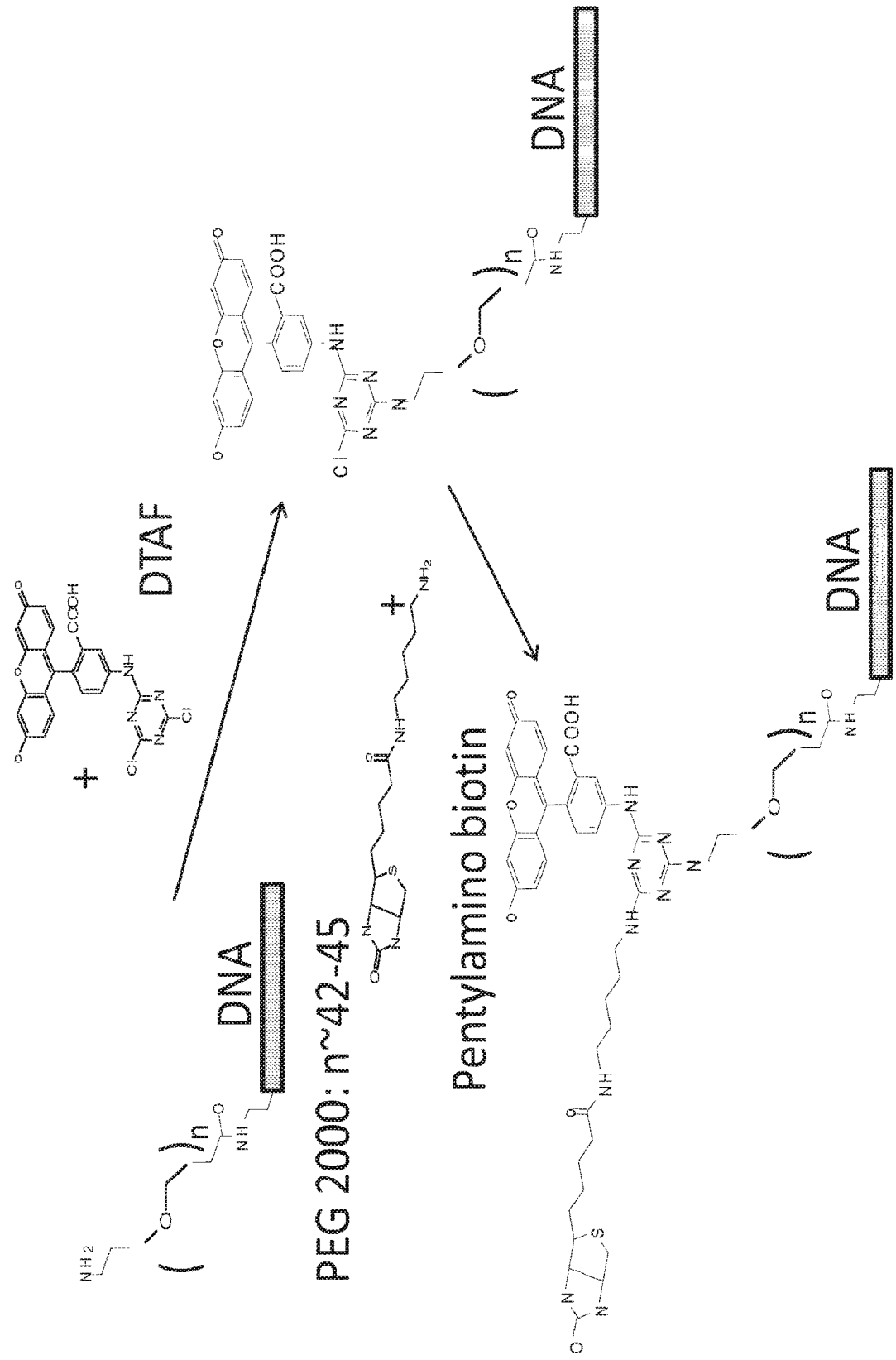
FIG. 12 is a schematic showing the steps in model library synthesis. DTAF was conjugated to amino-PEG modified headpiece (HP-1) in the first step. Following this step, a portion of HP-1-DTAF was further acylated with pentylamino-biotin.

After DTAF was coupled to HP-1, one more reactive group on the scaffold molecule is still available for modification. We chose an amino-biotin analog, EZ-Link Pentylamine-Biotin (Pierce), to couple at this position in order to generate a model binding compound (FIG. 12). The reaction was set up as follows. 20 μl of the reaction mixture contained around 200 μmol of HP-1-DTAF (Step 1) dissolved in 150 mM borate buffer, pH 9.5, and 10 nmol of pentylamine-biotin. The reaction was allowed to proceed for 4-12 hours at 75° C. The reaction was then purified by desalting on a Zeba spin column, as described above.

Step 3: Ligation of the DNA Tags to HP-1-DTAF-Biotin

Figure 13C:
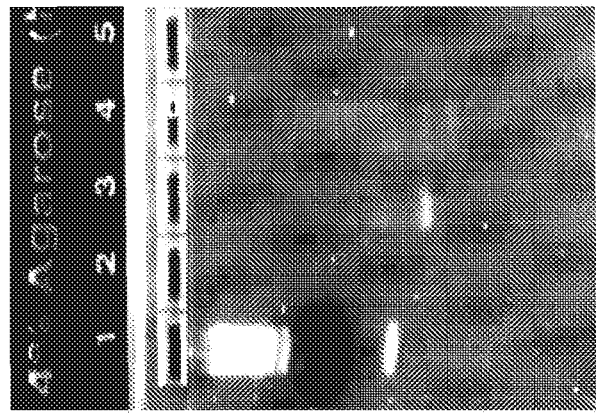
FIG. 13C illustrates PCR amplification (24 cycles) of the ligation reactions. M: marker (lowest band is 100); Lane 1: PCR amplification of the green fluorescent band from Lane 1 of FIG. 14B (HP-1-DTAF-biotin+Tag A); Lane 2: PCR amplification of the green fluorescent band from Lane 2 of FIG. 13B (HP-1-DTAF-biotin+all 3 tags and 3'-end oligo); Lane 3: PCR amplification of the crude ligation reaction HP-1-DTAF-biotin+all 3 tags; Lane 4: no template control.
Figure 13B:
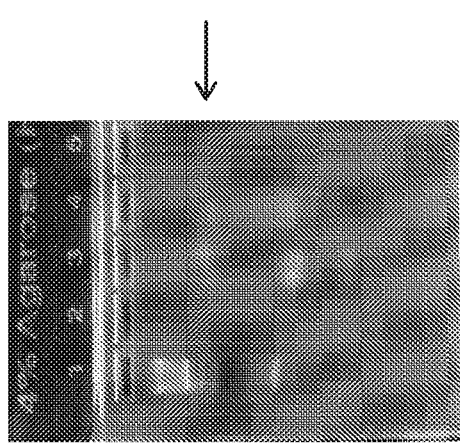
FIG. 13B illustrates a 4% agarose gel of HP-1-DTAF-biotin library at different steps of the DNA tag ligation. M: marker; Lane 1: HP-1-DTAF-biotin; Lane 2: 1+ Tag A only; Lane 3: 1+ Tags A, B, and C, as well as 3'-end oligo ligated. Arrow indicates bright green fluorescence (DTAF). No substantial separation is observed on the gel.
Figure 14B:
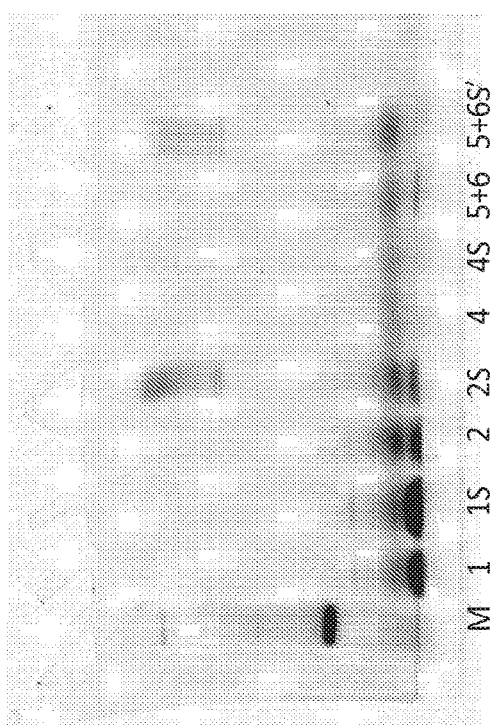
FIGS. 14A-D are a set of electrophoretic gels showing the purification of the XChem model compound and model selection (via a binding interaction between the biotin moiety of the XChem model compound and streptavidin). The gels are 4-12% SDS NuPage gels with MES running buffer. Gels were scanned for green fluorescence using a 450-nm laser.
Figure 14D:
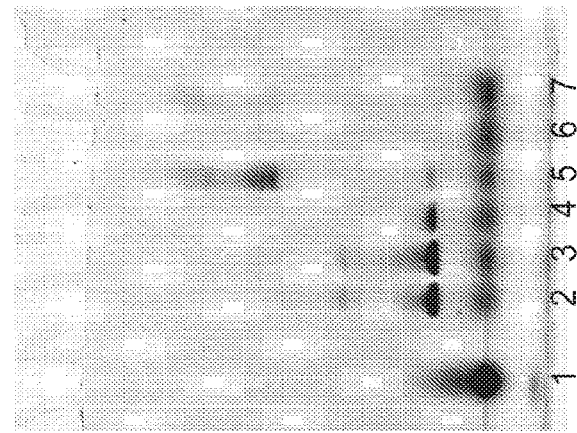
Figure 14A:
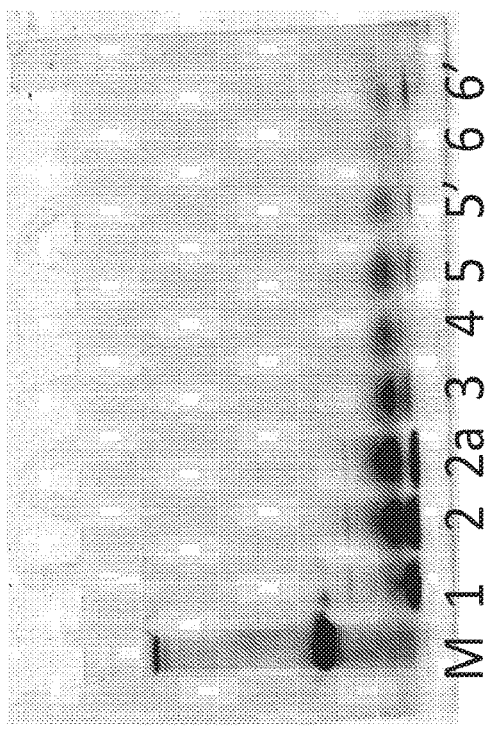
Figure 14C:
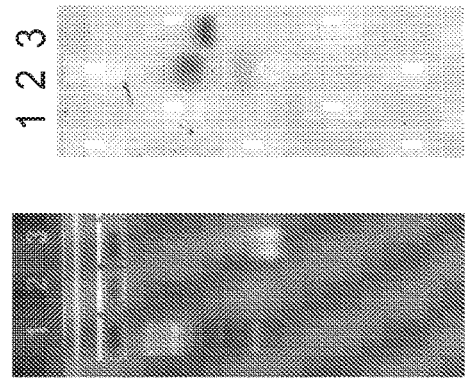

Phosphorylated DNA tags (3' end primer region and 5' and 3' PCR primers) were synthesized by IDT DNA. Oligonucleotide sequences (FIG. 13) are as follows.

```
DNA Tag A1 (top):
5'-phos-GGAGGACTGT              (SEQ ID NO: 53)

DNA Tag A1 (bottom):
5'-phos-AGTCCTCCGG              (SEQ ID NO: 54)

DNA Tag B1 (top):
5'-phos-CAGACGACGA              (SEQ ID NO: 55)

DNA Tag B1 (bottom):
5'-phos-GTCGTCTGAC              (SEQ ID NO: 56)

DNA Tag C1 (top):
5'-phos-CGATGCTCTT              (SEQ ID NO: 57)

DNA Tag C1 (bottom):
5'-phos-GAGCATCGTC              (SEQ ID NO: 58)

3' end (top):
5'-phos-GCTGTGCAGGTAGAGTGC-3'   (SEQ ID NO: 59)

3' end (bottom):
5'-AACGACACGTCCATCTCACG         (SEQ ID NO: 60)

5' PCR primer:
5'-CTCTCGCCTCAGCCAGGA           (SEQ ID NO: 61)

3' PCR primer:
5'-GCACTCTACCTGCACAGC           (SEQ ID NO: 62)
```

Equivalent amounts of top and bottom pairs of tags and 3' end oligonucleotides were dissolved in water and annealed by heating to 85° C. and ramping down to 4° C. in 200 mM NaCl, 50 mM Tris HCl, pH 7.0, buffer.

First, the double-stranded A1 tag was ligated to the headpiece. The ligation reaction (20 μl) contained 2.5 μM of HP-1-DTAF-biotin and 2.5 μM of double-stranded A1 tag in 1× T4 DNA ligase buffer and 60 Weiss units of T4 DNA ligase (New England BioLabs). The reaction was incubated at 16° C. for 16 hours. The resulting product did not resolve on any of the tested gels, including different percentages of TBE-urea, NativePage, SDS-PAGE, or 2% and 4% agarose E-gel (Invitrogen, Inc.). Mobility of the oligonucleotide, modified with PEG linker and DTAF-biotin, was mostly determined by the presence of these groups rather than by the DNA itself (data not shown). To test the efficiency of the ligation, we ligated all tags and 3' end oligonucleotides and performed PCR assays of the resulting construct to confirm the ligation efficiency. The ligation reaction (70 μl) contained: 2.5 μM of HP-1-DTAF-biotin; 2.5 μM of each of the annealed double-stranded DNA tags (A1, B1, and C1), as well as the 3' end tag; 1× T4 DNA ligase buffer; and 210 Weiss units of T4 DNA ligase. The reaction was incubated at 16° C. for 20 hours.

The reaction mixture was loaded on a 4% agarose gel and the fluorescent band was extracted from the gel. This material was used for the test 24 cycle PCR amplification using primers 5' and 3' as described above. The results are summarized in FIG. 13.

Step 4: Purification of HP-1-DTAF-Biotin on Streptavidin Beads and Reaction with Streptavidin Purification of HP-1-DTAF-biotin on streptavidin (SA) Dynal magnetic beads M-280 (Invitrogen) serves as a model for affinity selection for the chemical DNA-tagged library. SA beads were pre-equilibrated in 2× PBS buffer containing 0.05% Triton X-100. 50 μmol of HP-1-DTAF-biotin were loaded on 25 μl of the pre-washed SA beads for 15 minutes at room temperature with tumbling. The flow-through was collected and the beads were washed 3 times for 30 minutes with 1 ml of the same buffer. A final wash was performed at 80° C. for 10 minutes with 30 μl water (collected). The beads were eluted with 30 μl of 25 mM EDTA and 5 mM NaOH for 10 minutes at 90° C., and the eluent was immediately neutralized by adding 3 μl of 1 M Tris HCl, pH 7.0.

For the streptavidin binding experiment, 5 μl of the elution samples were incubated with an excess of streptavidin in 50 mM NaCl/10 mM Tris HCl, pH 7.0, for 10 minutes. The samples were mixed with gel-loading buffer without boiling and resolved on a 4-12% SDS NuPage gel (Invitrogen) using MES running buffer. The results are summarized in FIG. 14.

Example 4

Coupling of H(-Arg-εAhx)$_6$-Arg-OH Peptide to HP-1-DTAF

We have chosen an arginine-rich peptide R7, H(-Arg-εAhx)$_6$-Arg-OH (Bachem), to use as another modification for the last reactive group on the triazine scaffold. This is an arginine-aminohexanoic acid cell membrane permeable peptide used for intracellular compound delivery. The reaction was set up similar to the reaction conditions described above: 20 μl reaction contained around 200 μmol of HP-1-DTAF (Step 1) dissolved in 150 mM borate buffer, pH 9.5, and 10 nmol of R7 peptide. Under these conditions, the side chains of the arginines do not react, and the only reactive amine in the peptide is the N-terminus. The reaction was allowed to proceed for 12 hours at 75° C. and was then purified by desalting on a Zeba spin column.

Example 5

DNA Construct for Intracellular T7 RNAP Delivery Detection Experiment

The DNA construct used for the chemical "library of 1" intracellular delivery experiment was prepared from a PCR product of a VH DNA single clone of ~400 bp featuring a T7 promoter region at the 5' end and a short antibody constant Cmu region close to the 3' end of the molecule. In order to link the DNA construct to the modified headpiece of the model chemical library, a BsmI restriction site was appended upstream of the T7 promoter region by PCR amplification of the clone. BsmI restriction digest produced a 3' GG overhang, which allowed ligation to the headpiece (3' CC overhang). The 5' primer with BsmI site (underlined) was synthesized by IDT DNA, Inc.

```
                                          (SEQ ID NO: 63)
5'-GGATGCCGAATGCCTAATACGACTCACTATAGGG-
ACAATTACTATTTACAATTACA
```

Following PCR amplification, the DNA construct was purified using a PCR purification kit (Invitrogen), and the resulting DNA was digested with 250 U BsmI (New England BioLabs) at 65° C. in NEB buffer 4 for 2 hours. The DNA was purified on a 2% agarose gel. The ligation reaction (30 µl) contained 2 µmol of each VH DNA construct, digested with BsmI, as well as HP-1-DTAF-R7 (arginine-aminohexanoic acid peptide) in 1× T4 DNA ligase buffer and 60 Weiss units of T4 DNA ligase (New England BioLabs). The reaction was incubated at 16° C. for 20 hours. Due to high efficiency of the ligation, the material was further used for the intracellular delivery/T7 RNAP experiment without further purification. The results are summarized in FIG. 15.

Example 6

Synthesis of 10×10 Library

Step 1. Ligation of the Tag A to the Headpiece HP-T

In this exemplary library, only positions B and C are used. One tag A is ligated to HP-T. The tag has the following sequence:

```
DNA Tag A1 (top):
5'-phos-GGAGGACTGT         (SEQ ID NO: 64)

DNA Tag A1 (bottom):
5'-phos-AGTCCTCCGG         (SEQ ID NO: 65)
```

30 nmol of HP-T were mixed with 45 nmol of each Tag A1 top and Tag A1 bottom oligos in 1× T4 DNA ligase buffer and were annealed by heating to 95° C. for 1 minute, followed by cooling to 4° C. at 0.2° C./second. The sample was then brought to 16° C. 300 Weiss Units of T4 DNA ligase was added and the samples were allowed to incubate for 16-20 hours at 16° C. Following the ligation, HP-T-A was desalted using a Zeba column (Pierce). See, e.g., FIG. 16A.

Step 2. Ligation of Tags B1-812 and C Tags

Twelve ligation reactions were set up similar to the ligation reactions described above. In each of 12 tubes, 5 nmol pairs of B1-B12 top and bottom oligos were added to 1× T4 DNA ligase buffer and annealed as described above. HP-T-A was dissolved in 1× T4 DNA ligase buffer. 2.5 nmol of HP-T-A were aliquoted in these 12 tubes. 30 Weiss units of T4 DNA ligase were added to each tube and reactions were allowed to proceed for 20 hours at 16° C. Following the incubation, each reaction mixture was individually desalted on a 0.5 ml Zeba spin column, equilibrated with 150 mM borate buffer, pH 9.0. To each tube, a 20× excess of cyanouric chloride (50 nmol), dissolved in acetonitrile, was added and incubated for 1.5 hours at 4° C. Following this incubation, a 100× excess (250 nmol, i.e., 5× excess relative to cyanouric chloride) of amines B1-B12, dissolved in acetonitrile or DMF, was added in correspondence with the ligated B1-B12 tags. The reaction with amines was allowed to proceed for 20 hours at 4° C. Following this reaction the library was pooled, desalted twice on 2-ml Zeba columns and lyophilized. See, e.g., FIGS. 16B and 16C.

Like the reactions above, the C tags and amines are added using similar reaction conditions to those described above.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of producing a DNA-encoded chemical entity, the method comprising:
   (a) reacting a first functional group of a bifunctional linker to a first chemical building block, wherein the bifunctional linker has a single functional group that reacts with a chemical building block and a single functional group that reacts with a nucleotide, nucleotide analog, nucleoside, or nucleoside analog;
   (b) reacting the second functional group of the bifunctional linker to a single-stranded hairpin oligonucleotide, the hairpin oligonucleotide comprising (i) a self-complementary region and (ii) a single-stranded loop comprising at least one natural nucleoside or nucleoside analog, thereby forming a conjugate;
   (c) reacting a second chemical building block with the first chemical building block of the conjugate under conditions suitable for the formation of a covalent bond between the first chemical building block of the conjugate and the second chemical building block; and
   (d) ligating a first oligonucleotide tag to the single-stranded hairpin oligonucleotide of the conjugate, wherein the oligonucleotide tag comprises a region that encodes the identity of the first chemical building block and/or the identity of the second chemical building block, thereby forming a DNA-encoded chemical entity,
   wherein steps (a) and (b) and/or steps (c) and (d) can be performed in any order.

2. The method of claim 1, wherein the ligating of step (d) comprises nonenzymatic ligation.

3. The method of claim 1, wherein the oligonucleotide tag of step (d) comprises a fluorescent tag or a biotin label.

4. The method of claim 1, wherein the single-stranded hairpin oligonucleotide of step (b) comprises a region that encodes the identity of the first building block.

5. The method of claim 1, wherein the bifunctional linker is modified to increase solubility of the DNA-encoded chemical entity in organic conditions.

6. The method of claim 5, wherein the bifunctional linker comprises one or more of an alkyl chain, a polyethylene glycol unit, a branched species with positive charges, or a hydrophobic ring structure.

7. The method of claim 6, wherein the bifunctional linker comprises 12 to 45 polyethylene glycol units.

8. The method of claim 1, wherein the single-stranded hairpin oligonucleotide of step (b) and/or the oligonucleotide tag of step (d) are modified to increase solubility of the DNA-encoded chemical entity in organic conditions.

9. The method of claim 1, wherein the oligonucleotide tag of step (d) comprises a region that encodes the identity of the first chemical building block.

10. The method of claim 1, wherein the oligonucleotide tag of step (d) comprises a region that encodes the identity of the second chemical building block.

11. The method of claim 1, wherein the suitable conditions of step (c) comprise an organic solvent.

12. The method of claim 1, wherein the single-stranded loop of the hairpin oligonucleotide comprises a sequence that can serve as a primer-binding region for amplification.

13. The method of claim 1, wherein the bifunctional linker is attached at the 5' end of the single-stranded hairpin oligonucleotide of step (b); the bifunctional linker is embedded within the single-stranded hairpin oligonucleotide of step (b); or the bifunctional linker is placed in the middle of the single-stranded hairpin oligonucleotide of step (b).

14. The method of claim 13, wherein the bifunctional linker is attached at the 5' end of the single-stranded hairpin oligonucleotide of step (b).

15. The method of claim 13, wherein the bifunctional linker is embedded within the single-stranded hairpin oligonucleotide of step (b).

16. The method of claim 13, wherein the bifunctional linker is placed in the middle of the single-stranded hairpin oligonucleotide of step (b).

17. The method of claim 1, wherein the single-stranded hairpin oligonucleotide of step (b) comprises a T or C nucleotide comprising an aliphatic chain at the C5 position.

18. The method of claim 1, wherein the single-stranded hairpin oligonucleotide of step (b) comprises an azobenzene.

19. The method of claim 1, wherein the oligonucleotide tag of step (d) comprises a T or C nucleotide comprising an aliphatic chain at the C5 position.

20. The method of claim 9, wherein the method further comprises ligating a second oligonucleotide tag that encodes the identity of the second chemical building block to the first oligonucleotide tag.

21. The method of claim 20, wherein the method further comprises:
    (e) reacting a third chemical building block with the first chemical building block or the second chemical building block.

22. The method of claim 21, wherein the method further comprises:

(f) ligating a third oligonucleotide tag to the second oligonucleotide tag, wherein the third oligonucleotide tag encodes the identity of the third chemical building block, wherein steps (e) and (f) can be performed in any order.

23. The method of claim 1, wherein the method further comprises:
(e) reacting one or more additional chemical building blocks with a chemical building block of the conjugate.

24. The method of claim 23, wherein the method further comprises:
(f) ligating one or more oligonucleotide tags to the oligonucleotide tag of the conjugate, wherein each oligonucleotide tag encodes the identity of one of the one or more additional building blocks, wherein steps (e) and (f) can be performed in any order.

25. The method of claim 1, wherein the DNA-encoded chemical entity has an octanol:water coefficient from 1.0 to 2.5.

26. The method of claim 1, wherein the method produces a plurality of DNA-encoded chemical entities.

27. The method of claim 26, wherein the plurality comprises at least 1,000,000 different DNA-encoded chemical entities.

* * * * *

UNITED STATES PATENT AND TRADEMARK OFFICE
CERTIFICATE OF CORRECTION

| | |
|---|---|
| PATENT NO. | : 11,168,321 B2 |
| APPLICATION NO. | : 15/147600 |
| DATED | : November 9, 2021 |
| INVENTOR(S) | : Richard W. Wagner |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 342 days.

Signed and Sealed this
Thirteenth Day of December, 2022

Katherine Kelly Vidal
*Director of the United States Patent and Trademark Office*

SEQUENCE LISTING

```
<160> NUMBER OF SEQ ID NOS: 67

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctccggaga                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```
tccggaggac                                                           10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccggcgccga                                                           10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcgccggac                                                           10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccggtaccga                                                           10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtaccggac                                                           10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cccacgtgga                                                           10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cacgtgggac                                                              10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccgagctcga                                                              10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagctcggac                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccggatccga                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggatccggac                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccatcgatga                                                              10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atcgatggac                                                              10

```
<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccaagcttga                                                                 10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aagcttggac                                                                 10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccagatctga                                                                 10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agatctggac                                                                 10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgaattcga                                                                 10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaattcggac                                                                 10
```

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cctgatcaga                                                               10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgatcaggac                                                               10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cccatatgga                                                               10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catatgggac                                                               10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaacctgctt                                                               10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcaggttctc                                                               10

```
<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaagacgctt                                                              10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgtcttctc                                                              10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaccagactt                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtctggtctc                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gacgactctt                                                              10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagtcgtctc                                                              10

<210> SEQ ID NO 33
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gacgcttctt                                                              10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gaagcgtctc                                                              10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gagcaacctt                                                              10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggttgctctc                                                              10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gagccatctt                                                              10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gatggctctc                                                              10

<210> SEQ ID NO 39
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaaccactt                                                            10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtggttgctc                                                            10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcacagactt                                                            10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtctgtgctc                                                            10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcgatcactt                                                            10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtgatcgctc                                                            10

<210> SEQ ID NO 45
<211> LENGTH: 10
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 45
gcggttactt                                                              10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtaaccgctc                                                              10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcatgacctt                                                              10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtcatgctc                                                              10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcgtactctt                                                              10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gagtacgctc                                                              10

<210> SEQ ID NO 51
<211> LENGTH: 43
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: dT-C6-NH

<400> SEQUENCE: 51
tcctggctga ggcgagagtt tttctctcgc ctcagccagg acc                43

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: dT-C6-amino-PEG2000

<400> SEQUENCE: 52
tcctggctga ggcgagagtt tttctctcgc ctcagccagg acc                43

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggaggactgt                                                     10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agtcctccgg                                                     10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cagacgacga                                                     10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
```
gtcgtctgac                                                                  10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cgatgctctt                                                                  10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gagcatcgtc                                                                  10

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gctgtgcagg tagagtgc                                                         18

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gcactctacc tgcacagcaa                                                       20

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctctcgcctc agccagga                                                         18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcactctacc tgcacagc                                                         18

<210> SEQ ID NO 63
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggatgccgaa tgcctaatac gactcactat agggacaatt actatttaca attaca          56

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggaggactgt                                                              10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agtcctccgg                                                              10

<210> SEQ ID NO 66
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Z (benzyl carbamate)
<220> FEATURE:
<221> NAME/KEY: MISC_FEATURE
<222> LOCATION: (8)..(8)
<223> OTHER INFORMATION: Xaa is Osu (hydroxysuccinimide ester)

<400> SEQUENCE: 66

Xaa Gly Gly Gly Gly Gly Gly Xaa
1               5

<210> SEQ ID NO 67
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is Acp
<220> FEATURE:
<221> NAME/KEY: MISC_FEATURE
<222> LOCATION: (4)..(4)
<223> OTHER INFORMATION: Xaa is Acp
<220> FEATURE:
<221> NAME/KEY: MISC_FEATURE
<222> LOCATION: (6)..(6)

```
<223> OTHER INFORMATION: Xaa is Acp
<220> FEATURE:
<221> NAME/KEY: MISC_FEATURE
<222> LOCATION: (8)..(8)
<223> OTHER INFORMATION: Xaa is Acp
<220> FEATURE:
<221> NAME/KEY: MISC_FEATURE
<222> LOCATION: (10)..(10)
<223> OTHER INFORMATION: Xaa is Acp
<220> FEATURE:
<221> NAME/KEY: MISC_FEATURE
<222> LOCATION: (12)..(12)
<223> OTHER INFORMATION: Xaa is Acp

<400> SEQUENCE: 67

Arg Xaa Arg Xaa Arg Xaa Arg Xaa Arg Xaa Arg Xaa Arg
1               5                   10
```